United States Patent
Mizuguchi et al.

(10) Patent No.: US 9,141,755 B2
(45) Date of Patent: Sep. 22, 2015

(54) DEVICE AND METHOD FOR SELECTING GENES AND PROTEINS

(75) Inventors: Kenji Mizuguchi, Osaka (JP); Yian Chen, Osaka (JP); Lockesh Pati Tripathi, Osaka (JP)

(73) Assignee: NATIONAL INSTITUTE OF BIOMEDICAL INNOVATION, Ibaraki (JP)

( * ) Notice: Subject to any disclaimer, the term of this patent is extended or adjusted under 35 U.S.C. 154(b) by 942 days.

(21) Appl. No.: 13/219,272

(22) Filed: Aug. 26, 2011

(65) Prior Publication Data

US 2012/0054141 A1 Mar. 1, 2012

(30) Foreign Application Priority Data

Aug. 26, 2010 (JP) ................ 2010-188943

(51) Int. Cl.
*G06F 19/28* (2011.01)
*G06F 19/24* (2011.01)
*G06F 19/18* (2011.01)

(52) U.S. Cl.
CPC ............. *G06F 19/18* (2013.01); *G06F 19/28* (2013.01)

(58) Field of Classification Search
CPC  C12Q 1/6886; C12Q 2600/158; G06F 19/18; G06F 19/28; G06F 17/30864; G06F 19/12; G06F 19/22; G06F 19/20; G06F 19/24; G06F 17/30731; G06F 17/30873; G06F 19/10; G06N 5/022; G06N 5/02; G06N 7/055; G06N 5/00
See application file for complete search history.

(56) References Cited

FOREIGN PATENT DOCUMENTS

| JP | 2002-112793 | 4/2002 |
|---|---|---|
| JP | 2006-003970 | 1/2006 |
| JP | 2010-165230 | 7/2010 |

OTHER PUBLICATIONS

Kohji Moriishi et al. Critical role of PA28γ in hepatitis C virus-associated steatogenesis and hepatocarcinogenesis. PNAS, Jan. 30, 2007, vol. 104, No. 5, 1661-1666.
Yi-An Chen, Lokesh P. Tripathi, Kenji Mizuguchi, "TargetMine, an Integrated Data Warehouse for Candidate Gene Prioritisation and Target Discovery", PLoS ONE / www.plosone.org, Mar. 2011, vol. 6, Issue 3, p. 1-8.

*Primary Examiner* — John S Brusca
(74) *Attorney, Agent, or Firm* — Masuvalley & Partners

(57) ABSTRACT

The present invention provides a device, method and program for selecting genes or proteins from a set of candidate genes or proteins so that the selected genes or proteins have a stronger relevance to a specific subject. The device of the present invention contains a storage device, an input device and a processor. The storage device stores a data warehouse that contains a data about a collection of genes or proteins, with which annotations are associated. The input device receives an input of the set of candidate genes or proteins. The processor (a) gathers annotations that are associated with the candidate genes or proteins, (b) chooses annotations that are associated with the candidate genes or proteins more than a threshold number of times or frequencies, and (c) selects genes or proteins, with which at least one of the chosen annotations is associated.

17 Claims, 5 Drawing Sheets

DEVICE AND METHOD FOR SELECTING GENES AND PROTEINS

This patent application claims priority under 35 U.S.C. §119 to Japan patent application JP2010-188943, filed on Aug. 26, 2010, which is incorporated herein by reference.

TECHNICAL FIELD

The present invention relates to a device, a method and a computer program for selecting genes or proteins relevant to a given subject from a set of candidate genes or proteins.

BACKGROUND OF THE INVENTION

Knowledge about genes and proteins has been being accumulated due to recent developments of molecular biology. Many findings related to genes and proteins are now available through various public databases such as NCBI (National Center for Biotechnology Information), Entrez Gene, and DDBJ (DNA Data Bank of Japan).

Along with the development of public databases, technologies to predict functions of genes and proteins utilizing the information obtained from such databases have also been developed. For example, there is a method of determining G-protein coupled receptors based on amino acid sequences or nucleotide sequences (Japan Patent Application Publications JP2006-003970 and JP2002-112793). There is also a method of predicting protein-protein interactions based on a supervised machine-learning using characteristic vectors defined by attributes about protein structures and about drugs and compounds, which interact with proteins (Japan Patent Application Publication JP2010-165230).

SUMMARY OF THE INVENTION

Problem to be Solved by the Invention

Developments of microarray techniques have enabled to obtain comprehensive candidate genes that may have a specific function or relevancy. Since the number of candidate genes obtained is large, it is necessary to narrow down genes that are more likely to have a specific function or relevancy from the candidate genes. However, the technology to easily narrow down genes has not been established.

Methods of predicting protein functions using databases typically need a supervised machine-learning such as the method described in Japan Patent Application Publication JP2010-165230. Because the supervised machine-learning requires both positive examples and negative examples, this method cannot predict the function of a protein of which positive examples and negative examples are not obtained.

Means to Solve the Problem

One aspect of the present invention is a device for selecting genes or proteins relevant to a certain subject from a set of candidate genes or proteins. The device contains a storage device, an input device and a processor. The storage device stores a data warehouse that contains a biological data such as a collection of genes or proteins and annotations linked to the genes or proteins. The set of candidate genes or proteins is inputted into the device through the input device. The processor (a) gathers annotations associated with the candidate genes or proteins from the data warehouse or a database. Then, the processor (b) chooses annotations linked to the candidate genes or proteins more than a threshold number of times or frequencies from the gathered annotations. Lastly, the processor (c) selects genes or proteins, to which at least one of the chosen annotations is linked, from the set of candidate genes or proteins inputted.

The threshold number of times or frequencies is preferably set so that the annotations are linked to the candidate genes or proteins more frequently than to control genes or proteins with statistical significance. In other words, it is preferable to choose the annotations that associate with the candidate genes or proteins more frequently than with control genes or proteins with statistical significance such as p-value <0.05. Such arrangement improves the accuracy of the gene selection.

The processor may obtain a gene or protein that interacts with the candidate gene or protein from the data warehouse or database. And, the processor may add the obtained gene or protein to the set of candidate genes or proteins. Proteins interacting with each other often have or play a same biological function or role. The processor may obtain a gene or protein corresponding to the candidate gene or protein. Such obtained gene or protein may belong to a species different from a species of the candidate gene or protein. And, the processor may add the obtained gene or protein to the set of candidate genes or proteins. By increasing the number of candidate genes or proteins, the accuracy of the gene selection can be improved.

Another aspect of the present invention is a method of selecting genes or proteins from a set of candidate genes or proteins. This method is performed by a computer typically equipped with a storage device, an input device, a processor and an output device. In this method, (1) the computer receives an input of the set of candidate genes or proteins inputted through the input device. (2) The computer accesses a data warehouse or database that contains a data about a collection of genes or proteins, with which annotations are associated. (3) The computer gathers annotations that are associated with the candidate genes or proteins from the data warehouse or database. (4) Among the annotations gathered, the computer chooses annotations that are associated with the candidate genes or proteins more than a threshold number of times or frequencies. (5) The computer selects genes or proteins, with which at least one of the chosen annotations is associated, from the set of candidate genes or proteins. (6) The computer may output the selected genes or proteins from the output device. The data may be stored in the storage device. Or, the computer may access to a publicly available database through a network to acquire a necessary data while performing the method.

In the step (4), it is preferable that the computer chooses annotations that are associated with the candidate genes or proteins more frequently than with control genes or proteins with statistical significance. Examples of the control genes or proteins are a collection of genes or proteins derived from a tissue or an organism.

Another aspect of the present invention is a software run on a computer to select genes or proteins from a set of candidate genes or proteins. (1) The software makes the computer receive the set of candidate genes or proteins. (2) The software makes the computer access a data warehouse or database that contains a data about a collection of genes or proteins, with which annotations are associated. (3) The software makes the computer gather annotations that are associated with the candidate genes or proteins from the data warehouse or database. (4) The software makes the computer choose annotations that are associated with the candidate genes or proteins more than a threshold number of times or frequencies from the gathered annotations. And, (5) the software makes the computer select genes or proteins, with which at least one of the chosen annotations is associated, from the set of candidate genes or proteins. Further, (6) the software may make the computer output the selected genes or proteins.

The software may make the computer rank or sort the selected genes or proteins based on the number of the chosen annotations for each of the genes or proteins. In this case, the annotations can be weighed based on a number of times or frequencies the annotation is associated with the candidate genes or proteins.

Biological information related to the annotations may be selected from the group consisting of: gene information, gene homology information, genetic polymorphism information, gene expression information, protein information, protein-protein interaction information, information on biological functions of proteins, protein domain information, protein structure information, protein expression information, enzyme function information, pathway information, transcription factor information, information about genes that relate to diseases or disorders or that cause diseases or disorders, drug information, and compound information.

The genes or proteins to be selected are preferably directed toward a relevancy to a disease or disorder.

Effect of the Invention

The present invention provides a device and method for selecting the genes that are relevant to a specific subject from candidate genes. The present invention enables to easily pick up the genes relevant to, for example, a disease with higher possibility from comprehensive analytical results of microarrays and etc. In addition, the present invention enables to select the genes more easily because the present invention can select the genes without supervised machine-learning and does not need positive examples and negative examples.

DETAILED DESCRIPTION OF THE INVENTION

Figure 1:
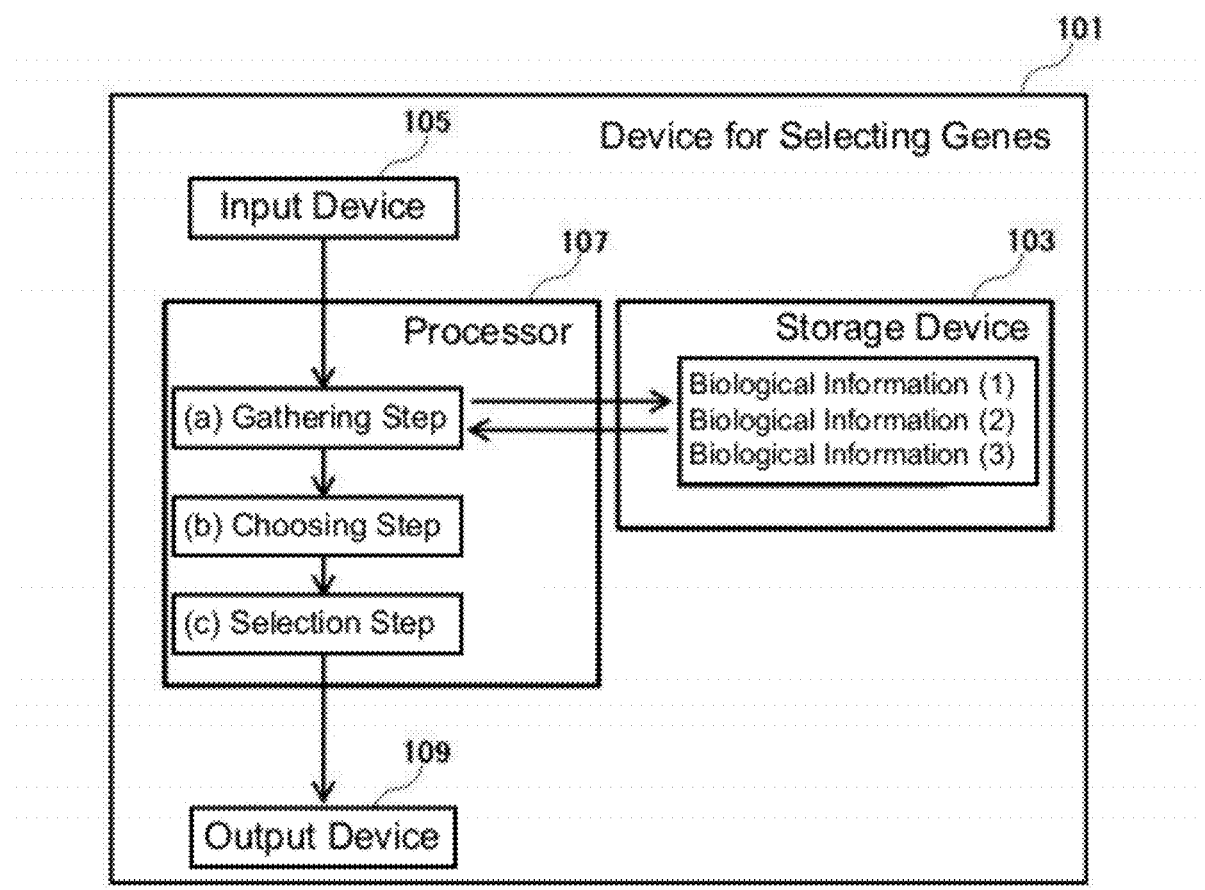
FIG. 1 is a block diagram showing an embodiment of the device of the present invention.

Below, the present invention is explained based on embodiments. However, the present invention is not limited to these embodiments.

One embodiment of the present invention can select genes that are relevant to a certain subject or relevant to each other from a set of candidate genes, using a data warehouse storing plural kinds of information about genes. The relevance here may be a relevance about functions and characteristics genes have. By the present invention, it is possible to narrow down genes, which may be related to a cause of a disease with higher probability, from a set of candidate genes.

Genes determine amino acid sequences of proteins that determine structures and functions of the proteins. Therefore, the subjects to be selected are proteins in other embodiment. Accordingly, the other embodiment can select proteins that are relevant to a certain subject or relevant to each other from a set of candidate proteins. Furthermore, utilizing the information on genes and proteins, it is possible to convert gene information into protein information and vice versa.

One embodiment is carried out using a data warehouse, which is stored in a storage device. The data warehouse is a system which stores multiple types of information and extracts necessary information from a set of the stored information.

The biological information stored in the data warehouse can be obtained from public databases. Examples of the public databases include NCBI (National Center for Biotechnology Information), Entrez Gene, UCSC (University of California Santa Cruz) database, DDBJ (DNA Data Bank of Japan), GeMDBJ, dbSNP, Ensembl, UniProtKB, InterPro, SIFTS, SCOP (Structural Classification of Proteins), PDB (Protein Data Bank), PPIview, BioGRID, KEEG (Kyoto Encyclopedia of Genes and Genomes), the Gene Ontology, UniProtKB-GOA, OregAnno (The Open Regulatory Annotation database), AMADEUS, Enzyme Nomenclature Database, OMIM (Online Mendelian Inheritance in Man), and ChEMBL. Other than the biological information from public databases, the biological information stored in the data warehouse may include biological information obtained from experiments or a literature search.

The data warehouse may store plural types of biological information such as (a) gene information, (b) gene homology information, (c) genetic polymorphism information, (d) gene expression information, (e) protein information, (f) protein-protein interaction information, (g) information on biological functions of proteins, (h) protein domain information, (i) protein structure information, (j) protein expression information, (k) enzyme function information, (l) pathway information, (m) transcription factor information, (n) information about genes that relate to diseases or disorders or that cause diseases or disorders, (o) drug information, and (p) compound information.

Below, the biological information is explained in more detail. The biological information generally contains descriptions about functions, structures and other features of genes and proteins.

(a) The gene information may contain a name of the gene, a symbol, an accession number, a nucleotide sequence of the gene, a name of the protein encoded by the gene, a protein ID, an amino acid sequence of the protein, a position of the gene in the genome, and related literatures. Such information can be assigned as genome annotations. The gene information can be obtained from public databases such as Entrez Gene, Ensembl and etc.

By storing the gene information, when a gene name is given, the corresponding accession number can be obtained. If a protein name or a protein ID is given, it is possible to obtain information of the gene encoding this protein and to convert the protein information into the gene information or vice versa.

(b) The gene homology information may be information showing a relation between the genes originated from a common ancestor. By using information on a homologous gene (orthologue) generated by a speciation or differentiation of species, the candidate gene can be converted to a corresponding gene of other species such as human, about which more information is provided, for example in the case the candidate gene is obtained from an animal model. The gene homology information can be obtained from public databases such as KEGG Orthology and etc.

(c) The genetic polymorphism information may be information on mutation in the gene sequence present at 1% of frequency or more in a population. The polymorphism information on the gene can be assigned as an annotation. The gene polymorphism information can be obtained from public databases such as GeMDBJ, dbSNP and etc.

(d) The gene expression information may contain information on gene expressions obtained by analyses in which animals or cells are exposed to a drug. It is possible to predict toxicity or analyze a mechanism of toxicity expression in a cellular level. The gene expression information, particularly gene expression information and toxicology information when mammals and mammalian cells are exposed to compounds, can be obtained from databases such as TG-GATEs (Toxicogenomics Project-Genomics Assisted Toxicity Evaluation system), Open TG-GATEs, which is an open edition of TG-GATEs, and etc.

(e) The protein information may contain a name of the protein, a protein ID, an amino acid sequence, a name of the gene encoding the protein, an accession number, a nucleotide sequence, a function of the protein, and related literatures. Such information can be assigned as protein annotation. The protein information can be obtained from public databases such as UniProtKB and etc.

By storing the protein information, when a protein name is given, the corresponding protein ID can be obtained. If a gene or a protein ID is given, it is possible to obtain information of the gene encoding this protein and to convert the protein information into the gene information or vice versa.

(f) The protein-protein interaction information may be information showing the relation of proteins whose interaction is identified by experiments such as yeast two-hybrid. Since proteins that interact with each other often have the same function or role, it is possible to gather proteins that interact with the candidate proteins and add these proteins to the candidate genes or proteins. Using the database of protein-protein interactions, an annotation about a protein that interacts with a candidate protein may be assigned to the candidate protein. The protein-protein interaction information can be obtained from public databases such as PPIview, BIOGRID and etc.

(g) The information on biological functions of proteins may be information showing the function of a protein in a living organism. Gene Ontology (GO) can be utilized for this information. In Gene Ontology, a protein is described by so-called GO Term classified into three types, Cellular Component, Biological Process, and Molecular Function. Using the database of Gene Ontology, the GO Term can be assigned to the candidate gene as an annotation. The gene ontology information can be obtained from public databases such as the Gene Ontology and UniProt KB GOA and etc.

(h) The protein domain information may be information containing a domain (a unit of sequence having an evolutionally common ancestor and having a common structure or a function) constituting a protein as well as its classification. The domain of the protein can be assigned to the candidate protein as an annotation. The protein domain information can be obtained from InterPro and etc.

(i) The protein structure information may include information related to a three-dimensional structure of the protein. Such three-dimensional structure information may include a volume of a ligand-binding portion of the protein, the number of constituting atoms, an area exposed to solvent, planarity, slenderness, curvature, hydrophobicity, the number of hydrogen bond donor atoms, the number of hydrogen bond acceptor atoms, amino acid composition on the surface of a ligand binding portion, a classification of a structural domain, and a cross-reference to protein information based on an amino acid sequence. The protein structure information can be obtained from public databases such as PDB (Protein Data Bank), SCOP (Structural Classification of Proteins), SIFTS and etc.

(j) The protein expression information may be information about proteins expressed in cells or tissues. It may include information obtained by proteomic analysis. The protein expression information can be obtained from public databases such as GeMDBJ (Genome Medicine Database of Japan) Proteomics and etc.

(k) The enzyme function information may be information of enzyme classification based on catalytic reactions. An Enzyme Commission (EC) number can be used for this information. The EC number of the enzyme function can be assigned to the candidate protein, whose enzymatic function is known, as an annotation. The enzyme function information can be obtained from public databases such as Enzyme Database and etc.

(l) The pathway information may be information showing a functional relation of the proteins or genes. From the pathway database, it is possible to obtain information on series of metabolic processes and interactions to which the protein or gene belong. A same annotation can be assigned to the genes or the proteins that belong to a same pathway. The pathway information can be obtained from public databases such as KEEG (Kyoto Encyclopedia of Genes and Genome) Pathway, Pathway Interaction Database and etc.

(m) The transcription factor information may be information showing a relation between a transcription factor and a gene this transcription factor interacts with. A transcription factor is a protein that binds to a specific regulatory region of a gene and regulates the gene expression. Using the database of transcription factor information, an annotation about a transcription factor that regulates the gene expression may be assigned to the candidate gene. The transcription factor information can be obtained from public databases such as OregAnno and etc.

(n) The information about genes that relate to diseases or disorders or that cause diseases or disorders may be information showing a disease or disorder caused by a genetic mutation or information showing a gene responsible for a disease or disorder. An annotation about a disease or disorder caused by a gene may be assigned to the candidate gene. The information about genes that relate to diseases or disorders or that cause diseases or disorders can be obtained from public databases such as OMIM (Online Mendelian Inheritance in Man), Disease Ontology, GWAS (Genome-wide association studies) and etc.

(o) The drug information may contain a general name of the drug, a product name, a chemical structure, and a target gene of the drug. Using the database of drug information, a drug that targets the gene may be assigned as an annotation to the candidate gene. The drug information can be obtained from public databases such as DrugBank and etc.

(p) The compound information may contain a dissociation constant and an inhibition constant of a low molecular weight compound that interacts with a protein. Using the database of compound information, a compound that interacts with the protein may be assigned as an annotation to the candidate protein. The compound information can be obtained from public databases such as ChEMBL and etc.

In one embodiment, plural kinds of information containing information mentioned above are stored in the data warehouse. Thus, plural kinds of information can be obtained about one gene or protein. Therefore, plural annotations can be assigning for one gene or protein. In other embodiment, such information does not have to be stored in the data warehouse, and such information may be timely obtained from public databases when necessary.

FIG. 1 is a block diagram showing a configuration of an embodiment of a device for selecting genes or proteins. The arrows in the figure indicate data flow. Below, the device for selecting genes or proteins is explained in detail, referring FIG. 1. The device 101 contains a storage device 103, an input device 105, a processor 107, and an output device 109. The storage device 103 stores a data warehouse containing plural kinds of biological information explained above.

An example of the device 101 is a computer, which can run a program of selecting genes or proteins. The device 101 can preferably access to internet so that it can access to public databases. An example of the storage device 103 is a hard disk drive installed in or connected to the device 101. An example of the input device 105 is a keyboard or a mouse connected to the device 101. An example of the processor 107 is a CPU (central processing unit) installed in the device 101. An example of the output device 109 is a display or a printer connected to the device 101.

The set of candidate genes are inputted into the device 101 through the input device 105. To input the candidate genes, the user can input information that is unique to the genes or that specifies the genes such as gene name, gene symbol, gene ID, accession number, or protein ID.

The set of candidate genes inputted may be the genes obtained from an experiment such as microarray or yeast two-hybrid. The microarray enables to detect a large number of gene expressions at one time. For example, it is possible to detect genes whose expression levels are different due to the presence or absence of a disease. These genes can be a set of candidate genes and can be a subject of the present invention to be narrowed down to select the genes likely relevant to the disease. The yeast two-hybrid is a method of investigating presences or absences of protein interactions. It is possible to screen proteins that interact with a certain protein. For example, it is possible to obtain a set of candidate genes that might be a cause of a disease if an experimenter screens proteins that interact with a protein known to be related to a disease.

The processor 107 may collect genes or proteins that interact with a candidate gene or protein from the data warehouse provided in the storage device 103 based on the protein-protein interaction information stored in the data warehouse. Further, the processor 107 may add the collected genes or proteins to the set of candidate genes or proteins. Or, the processor 107 may output the collected genes or proteins on the output device 109. In this case, the user may input the outputted genes or proteins to the device 101 for example after investigating the outputted genes. Further, the processor 107 may input the collected genes or proteins to itself as a set of candidate genes or proteins and proceed succeeding steps. Proteins that interact with a specific protein can be obtained from public databases such as PPIview, BioGrid and etc.

In the case the processor 107 compares annotations associated with the candidate genes or proteins and associated with the control genes or proteins in the later step, the computer may receive an input of a set of control genes or proteins. The set of control genes or proteins may be inputted by the user through the input device 105. Or, the device 101 may retrieve the set of control genes or proteins that is prepared beforehand and stored in the storage device 103. Furthermore, the set of control genes or proteins may be timely obtained from a public database. Alternatively, the set of control genes or proteins may be instantaneously generated randomly or following a certain algorithm.

Figure 5:
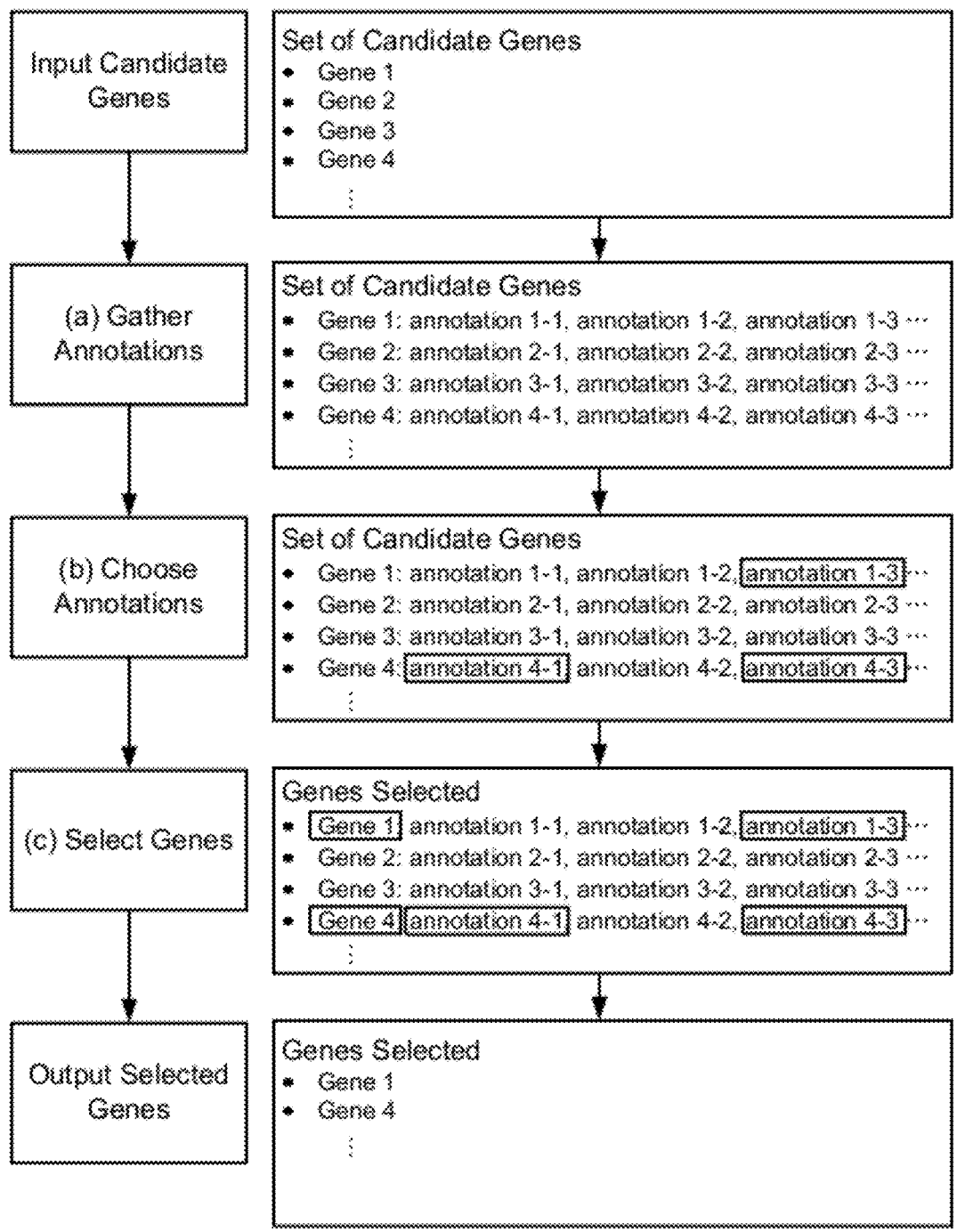
FIG. 5 is a flow chart and a schematic data structure chart showing steps and data arrangements of an embodiment of the present invention.

The processor 107 executes (a) a gathering step, (b) a choosing step, and (c) a selection step. Below, the steps (a)-(c) are explained in detail referring FIGS. 1 & 5.

(a) Gathering Step

In addition to the gene information, annotations related to biological information are stored in the data warehouse, and the annotations are assigned to the genes. Since plural kinds of biological information are stored in the data warehouse, plural annotations can be assigned to each of the genes. In this step, the processor 107 gathers annotations linked to the candidate genes from the storage device 103. In other embodiment, the processor 107 may access to a public database and remotely gather annotations associated with the candidate genes, using internet.

In the case the processor 107 compares annotations associated with the candidate genes or proteins and associated with the control genes or proteins in the next step, the computer may also gather annotations for the set of control genes or proteins.

After or during this step, the processor may remove redundancies of the gathered annotations. When the annotations are gathered from plural databases, particularly databases providing similar kinds of biological information, same annotations can be provided for one gene or protein. In other words, there can be duplicates of annotations for one gene or protein. The processor may deduplicate such annotations for each of the candidate genes or proteins. This can increase the accuracy of selecting genes or proteins. In other embodiment, redundancies of annotations may be removed before performing the steps. For example, redundancies of annotations can be removed after or during generating the data warehouse that is used for performing the present invention.

Prior to removing redundancies of the annotations, the processor may convert formats of the annotations to standard formats of annotations. Different databases sometimes use different formats of annotations to indicate the same annotation. This is often observed among annotations indicating compounds. By converting the annotation formats to the commonly used ones, the annotations that don't exactly match but indicate the same information can become the same annotations. For example, if the annotations are about compounds, it is possible to convert the descriptors contained in the annotation to InChI. Through the conversion, it is also possible to omit some information contained in the annotation. For example, by omitting information about chirality, two compounds, one of which contains chirality information and the other of which doesn't can be converted to be the same compound. Such kind of omission sometimes makes the gene selection more accurate.

In other embodiment, the processor may remove annotations that partially match with other annotation, or whose descriptors partially match with other annotation's. By a partial comparison, for example, two enantiomers can be regarded as one compound. In other embodiment, the processor may compare hash values of the annotations to remove redundancies of the gathered annotations. In other words, the processor may remove the annotations that have hash values same as other annotations'. Comparing hash values are sometimes more efficient than comparing annotations themselves particularly when the annotations contain structural data. Examples of the hash values include InChIKey.

(b) Choosing Step

In the choosing step, the processor 107 chooses the annotations that are more assigned to the candidate genes statistically significantly. Or, the processor 107 may choose annotations that are associated with the candidate genes more than a threshold number of times or frequencies. Such threshold can be determined by a statistical algorithm. For example, such threshold can be set so that the number of times or frequencies the annotation is assigned to the candidate genes is larger than the number of times or frequencies the annotation is assigned to control genes. In this case, it is preferable that being larger is statistically significant. An indicator of being statistically significant is that a p-value provided by a statistical significance test such as t-test or Fisher's exact test is less than a certain value such as 0.05 or 0.01 in a comparison of the number of times or frequencies the annotations are assigned to the candidate genes with the number of times or frequencies the annotations are assigned to the control genes. The set of control genes used to compare with the set of candidate genes may be an entire collection of genes of one species or whole genes expressed in a tissue.

For example, if a set of candidate genes is considered to be associated with an onset of a human disease, whole human genes may be used as a set of control genes. In this case, the statistical significance may be determined by comparing a percentage or frequency at which an annotation is assigned to the candidate genes with a percentage or frequency at which the annotation is assigned to the control genes, or whole human genes. It is also possible to set the number of control genes the same as the number of the candidate genes. In this case, the statistical significance may be determined by comparing the number of times an annotation is assigned to the candidate genes with the number of times the annotation is assigned to the control genes. Known statistical methods such as hypothesis test can be used to determine whether an annotation is assigned to the candidate genes with larger percentage or frequency than assigned to the control genes with a statistical significance.

In other embodiment, the threshold number of times or frequencies may be a predetermined value. In other word, the device 101 or a software that makes a computer perform this step may have such values internally as a predetermined value. Or, the device 101 may receive an input of such a threshold value from the user. When some types of information are used such as information on drugs that interact with proteins, choosing annotations based on a predetermined number of times the annotation is assigned to the candidate genes can provide more accurate results. In this case, the annotations chosen may be ranked or sorted based the numbers of times the annotations are assigned to the candidate genes.

In this step, one or plural kinds of annotations can be chosen. The more kinds of annotations chosen, the larger sensitivity (probability of selecting correct genes) of selecting genes but the smaller specificity (probability of not selecting incorrect genes) of selecting genes. On the other hand, if the types of annotations chosen are less, the sensitivity becomes smaller but the specificity becomes larger. Therefore, it is desirable to change the number of types of annotations to be chosen according to the candidate genes provided.

It is preferable to choose annotations from the annotations that give the largest difference between a percentage or frequency at which the annotations are assigned to the candidate genes and a percentage or frequency at which the annotations are assigned to the control genes. In other words, it is preferable to choose a certain number of top-ranked annotations from the annotations that give a larger difference between a percentage or frequency at which the annotations are assigned to the candidate genes and a percentage or frequency at which the annotations are assigned to the control genes. It is also possible to sort annotations so that the annotation assigned to the candidate genes with the largest percentage or frequency is placed at top and the annotation assigned to the candidate genes with the smallest percentage or frequency is placed at bottom. Furthermore, it is also possible to sort annotations from large to small based on the difference between a percentage or frequency at which the annotations are assigned to the candidate genes and a percentage or frequency at which the annotations are assigned to the control genes. Furthermore, it is also possible to sort annotations from small p-value to large p-value obtained by the comparison between a percentage or frequency at which the annotations are assigned to the candidate genes and a percentage or frequency at which the annotations are assigned to the control genes. Lower p-values obtained by the hypothesis test may be used as an indicator that the percentage or frequency at which the annotations are assigned to the candidate genes is larger than the percentage or frequency at which the annotations are assigned to the control genes. In this step, it is preferable to choose 1-10 types of most frequently assigned annotations for one kind of biological information from the annotations assigned to the candidate genes.

(c) Selection Step

In the selection step, the processor 107 selects genes, to which chosen annotations are assigned, from the candidate genes. The processor 107 may select the gene at least one chosen annotation is assigned to. Or, the processor 107 may only select the gene to which plural types of chosen annotations are assigned. Furthermore, the processor 107 may only select the gene to which plural types of chosen annotations are assigned with a specific combination.

When plural types of annotations are chosen in the previous step, it is possible to rank and sort the selected genes based on the number of chosen annotations assigned to the gene. In this case, it is possible to weigh the annotation based on a percentage or frequency at which the annotation is assigned to the candidate genes. It is also possible to weigh the annotation based on a difference between a percentage or frequency at which the annotation is assigned to the candidate genes and a percentage or frequency at which the annotation is assigned to the control genes.

The device 101 also contains an output device 109. The output device 109 outputs the genes or proteins selected in the previous step. The selected genes or proteins can be outputted through a display device such as display or a printing device such as printer.

The present invention also provides a method of selecting genes using a computer. An embodiment of the method selects genes or proteins relevant to a specific subject or relevant to each other from a set of candidate genes or proteins. The computer may have a storage device, an input device, and a processor. The storage device may store a data warehouse containing a data about a collection of genes or proteins, with which annotations are associated. In this method, (1) a set of candidate genes or proteins are inputted to the computer through the input device. (2) The processor gathers annotations that are assigned to the candidate genes or proteins inputted. The annotations are gathered from the data warehouse stored in the storage device. In other embodiment, the annotations may be gathered from a public database through internet. (3) The processor chooses annotations that are assigned to the candidate genes or proteins more than a threshold number of times or frequencies. The annotations are chosen from the gathered annotations. (4) The processor selects genes or proteins, to which at least one of the chosen annotations is assigned. The genes or proteins are selected from the set of candidate genes or proteins inputted.

In one embodiment, annotations may be chosen from the annotations that are assigned to the candidate genes or proteins statistically significantly more frequently than to control genes or proteins. In other embodiment, genes or proteins that interact with the candidate genes or proteins may be gathered from a data warehouse or database. The gathered genes or proteins may be added to the set of candidate genes or proteins.

The present invention also provides a computer program for making a computer select genes from the candidate genes. The present invention also provides a storage medium in which such computer program is stored. An embodiment of the computer program makes the computer select genes or proteins relevant to a specific subject or relevant to each other from a set of candidate genes or proteins. The program makes the computer gather annotations that are assigned to candidate genes or proteins from a data warehouse or database containing a data about a collection of genes or proteins, with which annotations are associated. The program makes the computer choose annotations that are assigned to the candidate genes or proteins statistically significantly more frequently than to the control genes or proteins. The program makes the computer select genes or proteins, to which at least one of the chosen annotations is assigned, from the set of candidate genes or proteins. Then, the program may make the computer output the selected genes or proteins.

EXAMPLES

Below, the present invention is explained in more detail based on Examples. However, the present invention is not limited to these Examples.

Example 1

Tests for Selecting Genes Using Genes Known to be Related to Diseases

Tests to select genes were performed using genes that are known to be related to the onsets of (1) pancreatitis, (2) hypercholesterolemia, (3) cirrhosis, and (4) cervical cancer.

In the data warehouse of this Example, information on biological functions of proteins, pathway information of proteins, and information about genes that cause diseases were stored. The information on biological functions of proteins was obtained from the Gene Ontology. The pathway information of proteins was obtained from KEEG Pathway. And, the information about genes that cause diseases was obtained from OMIM.

The genes already known to be related to the above diseases were defined as correct genes (about 30 genes). Genes twice as many as the correct genes were randomly selected. These genes were mixed with the correct genes and this mixture was inputted into a computer as a set of candidate genes. The lists of the genes inputted are shown in Tables 1-4.

TABLE 1

| (1) Pancreatitis | | | | | |
|---|---|---|---|---|---|
| Correct Genes (31 Genes) | | Randomly Selected Genes (62 Genes) | | | |
| Gene ID | Symbol | Gene ID | Symbol | Gene ID | Symbol |
| 1080 | ADH1B | 100128398 | LOC100128398 | 5052 | PRDX1 |
| 125 | ALDH2 | 100128927 | ZBTB42 | 51179 | HAO2 |
| 217 | CAT | 100287404 | LOC100287404 | 527 | ATP6V0C |
| 2944 | CD14 | 100292213 | LOC100292213 | 5281 | PIGF |
| 2947 | CFTR | 1016 | CDH18 | 54505 | DHX29 |
| 2950 | GSTM1 | 10521 | DDX17 | 55684 | C9orf86 |
| 2952 | GSTM3 | 10524 | KAT5 | 5651 | TMPRSS15 |
| 3105 | GSTP1 | 10531 | PITRM1 | 56979 | PRDM9 |
| 3106 | GSTT1 | 10857 | PGRMC1 | 57129 | MRPL47 |
| 3107 | HLA-A | 115350 | FCRL1 | 57561 | ARRDC3 |
| 3115 | HLA-B | 115560 | ZNF501 | 57824 | HMHB1 |
| 3119 | HLA-C | 148327 | CREB3L4 | 6943 | TCF21 |
| 3123 | HLA-DPB1 | 201895 | C4orf34 | 729475 | RAD51AP2 |
| 3265 | HLA-DQB1 | 2139 | EYA2 | 7593 | MZF1 |
| 3304 | HLA-DRB1 | 219464 | OR5T2 | 79058 | ASPSCR1 |
| 3458 | HRAS | 221416 | C6orf223 | 79692 | ZNF322A |
| 3586 | HSPA1B | 23111 | SPG20 | 79832 | QSER1 |
| 4257 | IFNG | 23406 | COTL1 | 8092 | ALX1 |
| 5444 | IL10 | 23423 | TMED3 | 81576 | CCDC130 |
| 3856 | KRT8 | 23456 | ABCB10 | 84103 | C4orf17 |
| 54576 | MGST1 | 2572 | GAD2 | 84293 | C10orf58 |
| 54577 | PON1 | 26094 | DCAF4 | 84634 | KISS1R |
| 54578 | PRSS1 | 26149 | ZNF658 | 84747 | UNC119B |
| 54658 | SOD2 | 2743 | GLRB | 84908 | FAM136A |
| 6648 | SPINK1 | 2967 | GTF2H3 | 84944 | MAEL |
| 5644 | TGFB1 | 374355 | C10orf96 | 8798 | DYRK4 |
| 6648 | TNF | 3762 | KCNJ5 | 8831 | SYNGAP1 |
| 7040 | UGT1A1 | 3797 | KIF3C | 90333 | ZNF468 |
| 7124 | UGT1A6 | 396 | ARHGDIA | 9541 | CIR1 |
| 847 | UGT1A7 | 401124 | DTHD1 | 9576 | SPAG6 |
| 929 | UGT1A8 | 4438 | MSH4 | 9940 | DLEC1 |

TABLE 2

(2) Hypercholesterolemia

| Correct Genes (32 Genes) | | Randomly Selected Genes (64 Genes) | | | |
| --- | --- | --- | --- | --- | --- |
| Gene ID | Symbol | Gene ID | Symbol | Gene ID | Symbol |
| 19 | ABCA1 | 100287510 | LOC100287510 | 3857 | KRT9 |
| 5243 | ABCB1 | 100287750 | LOC100287750 | 4212 | MEIS2 |
| 64240 | ABCG5 | 100288646 | LOC100288646 | 440093 | H3F3C |
| 64241 | ABCG8 | 100290804 | LOC100290804 | 50805 | IRX4 |
| 335 | APOA1 | 100294331 | LOC100294331 | 51063 | CALHM2 |
| 337 | APOA4 | 10539 | GLRX3 | 51460 | SFMBT1 |
| 116519 | APOA5 | 10855 | HPSE | 54902 | TTC19 |
| 338 | APOB | 11319 | ECD | 54925 | ZNF434 |
| 345 | APOC3 | 115207 | KCTD12 | 578 | BAK1 |
| 348 | APOE | 116448 | OLIG1 | 5893 | RAD52 |
| 1071 | CETP | 124801 | LSM12 | 60370 | AVPI1 |
| 1535 | CYBA | 135927 | C7orf34 | 64091 | POPDC2 |
| 1543 | CYP1A1 | 1360 | CPB1 | 64180 | DPEP3 |
| 1557 | CYP2C19 | 139604 | MAGEB16 | 65985 | AACS |
| 1559 | CYP2C9 | 146712 | B3GNTL1 | 6731 | SRP72 |
| 1565 | CYP2D6 | 148741 | ANKRD35 | 7130 | TNFAIP6 |
| 1576 | CYP3A4 | 158763 | ARHGAP36 | 727909 | LOC727909 |
| 1577 | CYP3A5 | 2053 | EPHX2 | 728299 | KRTAP19-8 |
| 1581 | CYP7A1 | 23630 | KCNE1L | 7508 | XPC |
| 2169 | FABP2 | 25902 | MTHFD1L | 79230 | ZNF557 |
| 3700 | ITIH4 | 25972 | UNC50 | 84261 | FBXW9 |
| 3949 | LDLR | 25976 | TIPARP | 84440 | RAB11FIP4 |
| 3990 | LIPC | 27006 | FGF22 | 8685 | MARCO |
| 4023 | LPL | 2784 | GNB3 | 8833 | GMPS |
| 10 | NAT2 | 28969 | BZW2 | 8884 | SLC5A6 |
| 255738 | PCSK9 | 28978 | TMEM14A | 89778 | SERPINB11 |
| 5444 | PON1 | 2960 | GTF2E1 | 9108 | MTMR7 |
| 5445 | PON2 | 308 | ANXA5 | 92370 | ACPL2 |
| 949 | SCARB1 | 3218 | HOXB8 | 93058 | COQ10A |
| 6720 | SREBF1 | 3222 | HOXC5 | 94235 | GNG8 |
| 6721 | SREBF2 | 326340 | ZAR1 | 9823 | ARMCX2 |
| 7099 | TLR4 | 340526 | RGAG4 | 9963 | SLC23A1 |

TABLE 3

(3) Cirrhosis

| Correct Genes (30 Genes) | | Randomly Selected Genes (60 Genes) | | | |
| --- | --- | --- | --- | --- | --- |
| Gene ID | Symbol | Gene ID | Symbol | Gene ID | Symbol |
| 125 | ADH1B | 64137 | ABCG4 | 100137047 | JMJD7 |
| 126 | ADH1C | 54 | ACP5 | 553128 | KIR2DL5B |
| 217 | ALDH2 | 642517 | AGAP9 | 100128942 | LOC100128942 |
| 718 | C3 | 83650 | AMAC1L2 | 100132963 | LOC100132963 |
| 1312 | COMT | 57037 | ANKMY2 | 6837 | MED22 |
| 1586 | CYP17A1 | 51382 | ATP6V1D | 51253 | MRPL37 |
| 1571 | CYP2E1 | 7920 | BAT5 | 64428 | NARFL |
| 2052 | EPHX1 | 79656 | BEND5 | 57727 | NCOA5 |
| 2950 | GSTP1 | 10902 | BRD8 | 51079 | NDUFA13 |
| 3077 | HFE | 26097 | C1orf77 | 123606 | NIPA1 |
| 3119 | HLA-DQB1 | 79680 | C22orf29 | 10361 | NPM2 |
| 3123 | HLA-DRB1 | 57545 | CC2D2A | 390152 | OR8H3 |
| 3162 | HMOX1 | 112869 | CCDC101 | 5090 | PBX3 |
| 3587 | IL10RA | 152206 | CCDC13 | 54510 | PCDH18 |
| 3552 | IL1A | 6369 | CCL24 | 56142 | PCDHA6 |
| 3553 | IL1B | 53841 | CDHR5 | 64063 | PRSS22 |
| 3569 | IL6 | 8099 | CDK2AP1 | 2185 | PTK2B |
| 3576 | IL8 | 1036 | CDO1 | 84839 | RAX2 |
| 55605 | KIF21A | 1116 | CHI3L1 | 64108 | RTP4 |
| 4049 | LTA | 1490 | CTGF | 6258 | RXRG |
| 4353 | MPO | 1653 | DDX1 | 6263 | RYR3 |
| 4843 | NOS2 | 80331 | DNAJC5 | 142891 | SAMD8 |
| 401 | PHOX2A | 8662 | EIF3B | 55532 | SLC30A10 |
| 5265 | SERPINA1 | 24147 | FJX1 | 9287 | TAAR2 |
| 6648 | SOD2 | 2319 | FLOT2 | 414059 | TBC1D3B |
| 6716 | SRD5A2 | 2539 | G6PD | 166655 | TRIM60 |
| 7037 | TFRC | 79802 | HHIPL2 | 7447 | VSNL1 |
| 7040 | TGFB1 | 8821 | INPP4B | 114049 | WBSCR22 |

TABLE 3-continued (3) Cirrhosis

| Correct Genes (30 Genes) | | Randomly Selected Genes (60 Genes) | | | |
|---|---|---|---|---|---|
| Gene ID | Symbol | Gene ID | Symbol | Gene ID | Symbol |
| 7124 | TNF | 117283 | IP6K3 | 7474 | WNT5A |
| 7132 | TNFRSF1A | 3714 | JAG2 | 51538 | ZCCHC17 |

TABLE 4

(4) Cervical Cancer

| Correct Genes (37 Genes) | | Randomly Selected Genes (74 Genes) | | | |
|---|---|---|---|---|---|
| Gene ID | Symbol | Gene ID | Symbol | Gene ID | Symbol |
| 5243 | ABCB1 | 51099 | ABHD5 | 100294156 | LOC100294156 |
| 477 | ATP1A2 | 9068 | ANGPTL1 | 376132 | LRRC10 |
| 627 | BDNF | 79642 | ARSJ | 84061 | MAGT1 |
| 773 | CACNA1A | 23192 | ATG4B | 2847 | MCHR1 |
| 8912 | CACNA1H | 7809 | BSND | 4193 | MDM2 |
| 1137 | CHRNA4 | 55727 | BTBD7 | 4548 | MTR |
| 1476 | CSTB | 55009 | C19orf24 | 4584 | MUC3A |
| 1557 | CYP2C19 | 51149 | C5orf45 | 7080 | NKX2-1 |
| 1559 | CYP2C9 | 23705 | CADM1 | 4900 | NRGN |
| 1621 | DBH | 892 | CCNC | 645974 | PABPC1L2B |
| 11083 | DIDO1 | 124599 | CD300LB | 389860 | PAGE2B |
| 2550 | GABBR1 | 51362 | CDC40 | 401 | PHOX2A |
| 2558 | GABRA5 | 22856 | CHSY1 | 5359 | PLSCR1 |
| 2560 | GABRB1 | 1178 | CLC | 7799 | PRDM2 |
| 2562 | GABRB3 | 1339 | COX6A2 | 27166 | PRELID1 |
| 2563 | GABRD | 6376 | CX3CL1 | 57580 | PREX1 |
| 2566 | GABRG2 | 1644 | DDC | 5806 | PTX3 |
| 2897 | GRIK1 | 9879 | DDX46 | 50700 | RDH8 |
| 3123 | HLA-DRB1 | 50514 | DEC-1. | 55298 | RNF121 |
| 3240 | HP | 1742 | DLG4 | 6135 | RPL11 |
| 3553 | IL1B | 2108 | ETFA | 6318 | SERPINB4 |
| 3766 | KCNJ10 | 54827 | FAM55D | 341880 | SLC35F4 |
| 3760 | KCNJ3 | 91893 | FDXACB1 | 27173 | SLC39A1 |
| 3763 | KCNJ6 | 143162 | FRMPD2 | 339745 | SPOPL |
| 3765 | KCNJ9 | 344758 | GPR149 | 23380 | SRGAP2 |
| 3785 | KCNQ2 | 25988 | HINFP | 10910 | SUGT1 |
| 3786 | KCNQ3 | 3013 | HIST1H2AD | 64420 | SUSD1 |
| 10656 | KHDRBS3 | 220988 | HNRNPA3 | 7006 | TEC |
| 163175 | LGI4 | 29911 | HOOK2 | 25976 | TIPARP |
| 4128 | MAOA | 3803 | KIR2DL2 | 124491 | TMEM170A |
| 4988 | OPRM1 | 440021 | KRTAP5-2 | 7158 | TP53BP1 |
| 5080 | PAX6 | 89782 | LMLN | 136541 | TRYX3 |
| 5173 | PDYN | 100130764 | LOC100130764 | 10628 | TXNIP |
| 6323 | SCN1A | 100131539 | LOC100131539 | 29089 | UBE2T |
| 6324 | SCN1B | 100289169 | LOC100289169 | 25989 | ULK3 |
| 6508 | SLC4A3 | 100290528 | LOC100290528 | 55625 | ZDHHC7 |
| 7515 | XRCC1 | 100292448 | LOC100292448 | 100131980 | ZNF705G |

Based on the information on biological functions of proteins (the Gene Ontology), the pathway information of proteins (KEEG Pathway), and the information about genes that cause diseases (OMIM), a processor executed the gathering step and collected annotations assigned to the candidate genes inputted. The number (number and number of types) of annotations gathered for each disease is shown in Table 5.

TABLE 5

| | The Gene Ontology | KEEG Pathway | OMIM | Total |
|---|---|---|---|---|
| (1) Pancreatitis | 294 annotations | 289 annotations | 53 annotations | 636 annotations |
| | 242 types | 120 types | 45 types | 407 types |
| (2) Hypercholesterolemia | 92 annotations | 92 annotations | 41 annotations | 534 annotations |
| | 47 types | 47 types | 36 types | 341 types |
| (3) Cirrhosis | 441 annotations | 232 annotations | 55 annotations | 728 annotations |
| | 341 types | 113 types | 50 types | 504 types |

TABLE 5-continued

|  | The Gene Ontology | KEEG Pathway | OMIM | Total |
|---|---|---|---|---|
| (4) Cervical Cancer | 239 annotations 195 types | 122 annotations 89 types | 67 annotations 64 types | 428 annotations 348 types |

Next, the processor executed the choosing step. The number of annotation assignments for the candidate genes was compared with the number of assignments for entire human genome, and it was determined as statistically significantly larger number when the p-value obtained by the comparison was smaller than a threshold value 0.05, or p<0.05. The top 10 annotations that gave the largest number differences between for the candidate genes and for the entire human genome are shown in Tables 6-9. The annotations were sorted so that the annotation having a larger difference (smaller p-value) comes to the upper side. When the number of the annotations with p<0.05 was less than ten, all the annotations that provided p<0.05 are shown in the table.

TABLE 6

(1) Pancreatitis

| ID | Description of Annotation | p-value |
|---|---|---|
| the Gene Ontology | | |
| GO: 0002740 | negative regulation of cytokine secretion during immune response | 0.01773084 |
| GO: 0030656 | regulation of vitamin metabolic process | 0.01773084 |
| GO: 0045191 | regulation of isotype switching | 0.01773084 |
| GO: 0060556 | regulation of vitamin D biosynthetic process | 0.01773084 |
| GO: 0046136 | positive regulation of vitamin metabolic process | 0.01792347 |
| GO: 0060557 | positive regulation of vitamin D biosynthetic process | 0.01792347 |
| GO: 0051707 | response to other organism | 0.01934053 |
| GO: 0050896 | response to stimulus | 0.02025122 |
| GO: 0002374 | cytokine secretion during immune response | 0.02074739 |
| GO: 0002739 | regulation of cytokine secretion during immune response | 0.02074739 |
| KEEG Pathway | | |
| 05330, | Allograft rejection | 1.09E−09 |
| 04940, | Type I diabetes mellitus | 2.11E−09 |
| 00980, | Metabolism of xenobiotics by cytochrome P450 | 2.74E−09 |
| 00982, | Drug metabolism - cytochrome P450 | 2.74E−09 |
| 05332, | Graft-versus-host disease | 2.14E−08 |
| 04612, | Antigen processing and presentation | 1.07E−07 |
| 05320, | Autoimmune thyroid disease | 2.45E−06 |
| 00053, | Ascorbate and aldarate metabolism | 1.44E−05 |
| 05140, | Leishmaniasis | 1.49E−05 |
| 05310, | Asthma | 4.17E−05 |
| OMIM | | |
| 167800 | PANCREATITIS, HEREDITARY; PCTT | 2.08E−04 |
| 106300 | SPONDYLOARTHROPATHY, SUSCEPTIBILITY TO, 1; SPDA1 | 0.001298 |
| 219700 | CYSTIC FIBROSIS; CF | 0.001298 |
| 608579 | SEVERE CUTANEOUS ADVERSE REACTION, SUSCEPTIBILITY TO | 0.001298 |
| 126200 | MULTIPLE SCLEROSIS, SUSCEPTIBILITY TO; MS | 0.014955 |
| 131300 | CAMURATI-ENGELMANN DISEASE | 0.021428 |
| 143500 | GILBERT SYNDROME | 0.021428 |
| 176400 | PRECOCIOUS PUBERTY, CENTRAL | 0.021428 |
| 218800 | CRIGLER-NAJJAR SYNDROME | 0.021428 |
| 226200 | ENTEROKINASE DEFICIENCY | 0.021428 |

TABLE 7

(2) Hypercholesterolemia

| ID | Description of Annotation | p-value |
|---|---|---|
| the Gene Ontology | | |
| GO: 0055088 | lipid homeostasis | 3.64E−20 |
| GO: 0042632 | cholesterol homeostasis | 8.10E−19 |
| GO: 0055092 | sterol homeostasis | 8.10E−19 |
| GO: 0015918 | sterol transport | 5.48E−15 |
| GO: 0030301 | cholesterol transport | 5.48E−15 |
| GO: 0010876 | lipid localization | 1.37E−13 |
| GO: 0034367 | macromolecular complex remodeling | 3.19E−13 |
| GO: 0034368 | protein-lipid complex remodeling | 3.19E−13 |

TABLE 7-continued

(2) Hypercholesterolemia

| ID | Description of Annotation | p-value |
|---|---|---|
| GO: 0034369 | plasma lipoprotein particle remodeling | 3.19E−13 |
| GO: 0006869 | lipid transport | 4.66E−13 |
| KEEG Pathway | | |
| 03320, | PPAR signaling pathway | 4.02E−04 |
| 00591, | Linoleic acid metabolism | 0.00114728 |
| 00830, | Retinol metabolism | 0.00132439 |
| 00982, | Drug metabolism - cytochrome P450 | 0.00138283 |
| 00980, | Metabolism of xenobiotics by cytochrome P450 | 0.00151521 |
| 02010, | ABC transporters | 0.00197428 |
| 00983, | Drug metabolism - other enzymes | 0.00297042 |
| 00140, | Steroid hormone biosynthesis | 0.00345192 |
| 00590, | Arachidonic acid metabolism | 0.03871049 |
| 03320, | PPAR signaling pathway | 4.02E−04 |
| OMIM | | |
| 143890 | HYPERCHOLESTEROLEMIA, AUTOSOMAL DOMINANT | 1.54E−05 |
| 210250 | SITOSTEROLEMIA | 0.00141227 |
| 604091 | HYPOALPHALIPOPROTEINEMIA, PRIMARY | 0.00141227 |
| 152430 | LONGEVITY 1 | 0.00622191 |
| 104310 | ALZHEIMER DISEASE 2 | 0.01611205 |
| 143470 | HYPERALPHALIPOPROTEINEMIA | 0.01611205 |
| 144010 | HYPERCHOLESTEROLEMIA, AUTOSOMAL DOMINANT, TYPE B | 0.01611205 |
| 144650 | HYPERLIPOPROTEINEMIA, TYPE V | 0.01611205 |
| 205400 | TANGIER DISEASE; TGD | 0.01611205 |
| 233690 | GRANULOMATOUS DISEASE, CHRONIC, AUTOSOMAL RECESSIVE, CYTOCHROME b-NEGATIVE | 0.01611205 |

TABLE 8

(3) Cirrhosis

| ID | Description of Annotation | p-value |
|---|---|---|
| the Gene Ontology | | |
| GO: 0042033 | chemokine biosynthetic process | 2.73E−05 |
| GO: 0050755 | chemokine metabolic process | 2.73E−05 |
| GO: 0045073 | regulation of chemokine biosynthetic process | 2.74E−05 |
| GO: 0032103 | positive regulation of response to external stimulus | 3.46E−05 |
| GO: 0001819 | positive regulation of cytokine production | 4.81E−05 |
| GO: 0001816 | cytokine production | 5.63E−05 |
| GO: 0010573 | vascular endothelial growth factor production | 6.32E−05 |
| GO: 0010574 | regulation of vascular endothelial growth factor production | 6.32E−05 |
| GO: 0045080 | positive regulation of chemokine biosynthetic process | 1.02E−04 |
| GO: 0042035 | regulation of cytokine biosynthetic process | 1.06E−04 |
| KEEG Pathway | | |
| 5140 | Leishmaniasis | 6.93E−06 |
| 4940 | Type I diabetes mellitus | 2.85E−05 |
| 5142 | Chagas disease | 3.25E−05 |
| 5332 | Graft-versus-host disease | 4.36E−05 |
| 4060 | Cytokine-cytokine receptor interaction | 4.55E−04 |
| 5144 | Malaria | 6.57E−04 |
| 4640 | Hematopoietic cell lineage | 7.08E−04 |
| 980 | Metabolism of xenobiotics by cytochrome P450 | 0.0022224 |
| 350 | Tyrosine metabolism | 0.0028146 |
| 4672 | Intestinal immune network for IgA production | 0.0054005 |
| OMIM | | |
| 248310 | PLASMODIUM FALCIPARUM BLOOD INFECTION LEVEL | 0.02070852 |
| 606963 | PULMONARY DISEASE, CHRONIC OBSTRUCTIVE | 0.02094706 |
| 108010 | ARTERIOVENOUS MALFORMATIONS OF THE BRAIN | 0.02137742 |
| 131300 | CAMURATI-ENGELMANN DISEASE | 0.02137742 |
| 135700 | FIBROSIS OF EXTRAOCULAR MUSCLES, CONGENITAL, 1; CFEOM1 | 0.02137742 |
| 142680 | PERIODIC FEVER, FAMILIAL, AUTOSOMAL DOMINANT | 0.02137742 |
| 148000 | KAPOSI SARCOMA | 0.02137742 |
| 167870 | PANIC DISORDER 1; PAND1 | 0.02137742 |
| 176100 | PORPHYRIA CUTANEA TARDA | 0.02137742 |
| 190000 | TRANSFERRIN; TF | 0.02137742 |

TABLE 9

(4) Cervical Cancer

| ID | Description of Annotation | p-value |
|---|---|---|
| | KEEG Pathway | |
| 4080 | Neuroactive ligand-receptor interaction | 0.00307 |
| | OMIM | |
| 604233 | GENERALIZED EPILEPSY WITH FEBRILE SEIZURES PLUS; GEFS+ | 6.79E−04 |
| 607208 | SEVERE MYOCLONIC EPILEPSY OF INFANCY; SMEI | 0.0063733 |
| 104290 | ALTERNATING HEMIPLEGIA OF CHILDHOOD | 0.0213162 |
| 106210 | ANIRIDIA; AN | 0.0213162 |
| 108500 | EPISODIC ATAXIA, TYPE 2; EA2 | 0.0213162 |
| 118700 | CHOREA, BENIGN HEREDITARY; BHC | 0.0213162 |
| 120430 | COLOBOMA OF OPTIC NERVE | 0.0213162 |
| 121200 | EPILEPSY, BENIGN NEONATAL, 1; EBN1 | 0.0213162 |
| 121201 | EPILEPSY, BENIGN NEONATAL, 2; EBN2 | 0.0213162 |
| 129750 | ECTOPIA PUPILLAE | 0.0213162 |

In the choosing step, annotations were chosen from the annotations that had larger difference from the control, in other words, that had lower p-value. The number of annotations chosen was varied from one to ten types.

Next, the processor executed a selection step and selected the genes to which at least one annotation chosen was assigned. Then, the selected genes were outputted from an output device. An example of the output result is shown in Table 10, which shows the gene IDs of the genes selected by the selection step when the top ranked annotation about the (1) pancreatitis is chosen in the choosing step.

TABLE 10

| Annotation Chosen (ID) | | Genes Selected (ID) |
|---|---|---|
| the Gene Ontology | GO: 0002740 | 3586, 7124 |
| KEEG Pathway | 05330 | 3105, 3106, 3107, 3115, 3119, 3123, 3458, 3586, 7124 |
| OMIM | 167800 | 1080, 5644, 6690 |

Figure 2:
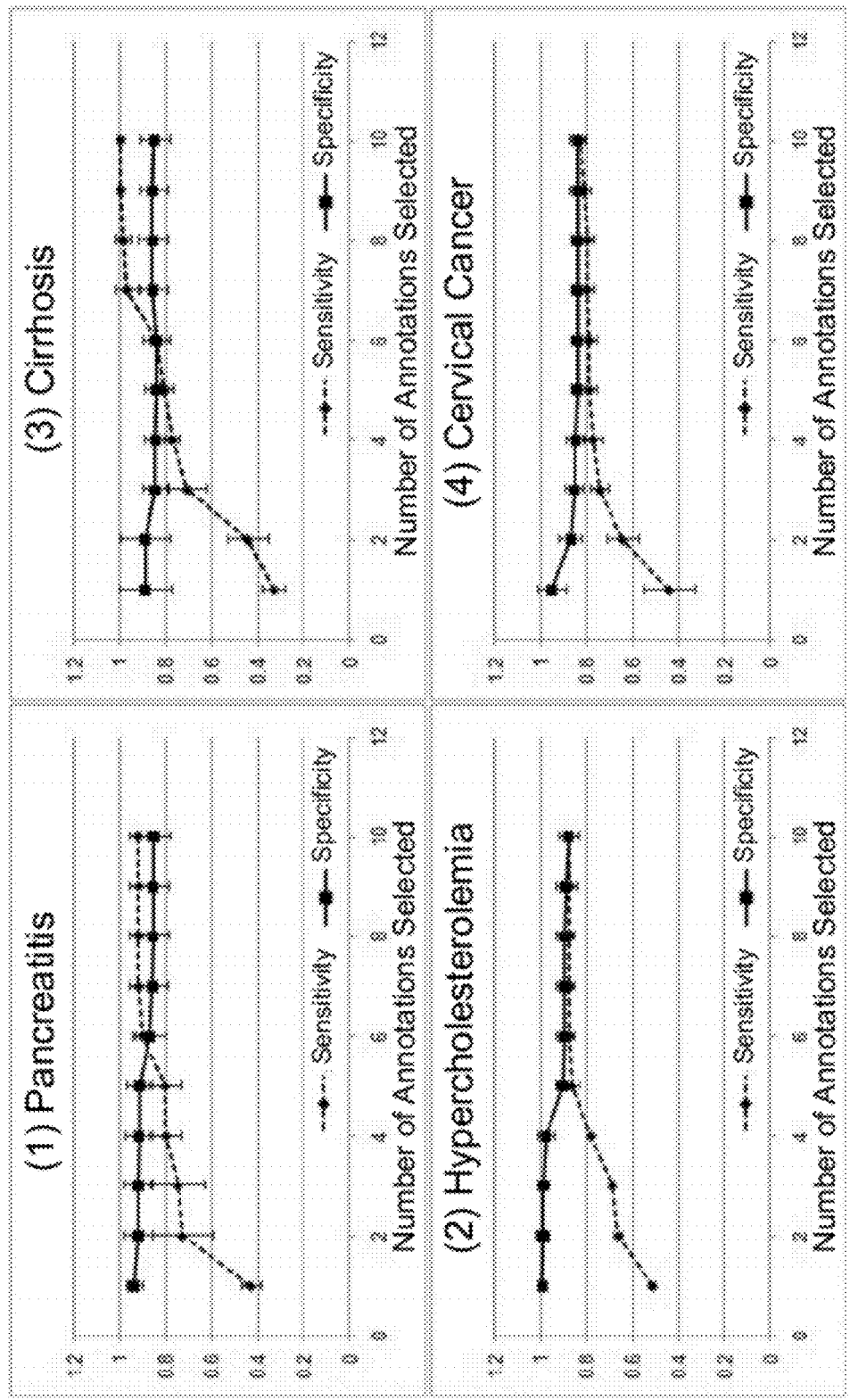
FIG. 2 is a graph showing sensitivities and specificities in the tests using the present invention.

The above-described steps from random gene selection to selecting genes were repeated ten times. FIG. 2 shows the average sensitivities and specificities on the genes outputted as the genes related to the disease. The average sensitivities and specificities are the averages of ten times of the repetition. The horizontal axis of the graph shows the number of annotations chosen in the choosing step. For all the diseases, the correct genes were outputted with about 80% of sensitivity and specificity.

Example 2

Selecting New Genes Related to a Disease

Using the device of the present invention, genes related to an onset of hepatitis C was selected. Although it has been known that an interaction between a hepatitis C virus (HCV) Core protein and human protein PA28γ is important for the onset of hepatitis C (Moriishi, K. et al., "Critical role of PA28γ in hepatitis C virus-associated steatogenesis and hepatocarcinogenesis.", P.N.A.S., 2007), the detailed mechanism has yet been unknown and human genes relevant to the onset of hepatitis C have not been identified. Therefore, candidate genes were narrowed down using the present invention.

Information stored in the data warehouse was protein-protein interaction information, information on biological functions of proteins, pathway information of proteins, and information about genes that relate to or cause diseases. The protein-protein interaction information was obtained from BioGrid and PPIview. The information on biological functions of proteins was obtained from the Gene Ontology. The pathway information of proteins was obtained from KEEG Pathway. And, the information about genes that relate to or cause diseases was obtained from OMIM and Disease Ontology.

By yeast two-hybrid, proteins that interacted with the HCV Core or NS4B were screened in the host using Human Adult liver library (product of MoBiTec Inc.). As a result of screening, 11 proteins that interacted with Core and 45 proteins that interacted with NS4B were identified. The identified proteins are shown in Tables 11 & 12.

TABLE 11

| Gene ID | Symbol | Description of the Gene |
|---|---|---|
| 1937 | EEF1G | Eukaryotic translation elongation factor 1 gamma |
| 1964 | EIF1AX | Eukaryotic translation initiation factor 1A, X-linked |
| 2023 | ENO1 | Enolase 1, (Alpha) |
| 2109 | EFTB | Electoron-transfer-flavoprotein, beta polypeptide |
| 2512 | FTL | Ferritin, light polypeptide |
| 292 | SLC25A5 | Solute carrier family 25 (mitochondrial carrier; adenine nucleotide translocator), member 5 |
| 4720 | NDUFS2 | NADH dehydrogenase (ubiquinone) Fe—S protein 2, 49 kDa (NADH-coenzyme Q reductase) |
| 5265 | SERPINA1 | Serpin peptidase inhibitor, clade A (alpha-1 antiproteinase, antitrypsin), member 1 |
| 5688 | PSMA7 | Proteosome (prosome, macropain) subunit, alpha type, 7 |
| 81502 | HM13 | Histocompatibility (minor) 13 |
| 9804 | TOMM20 | Translocase of outer mitochondrial membrane 20 homolog (yeast) |

TABLE 12

| Gene ID | Symbol | Description of the Gene |
|---|---|---|
| 10130 | PDIA6 | Protein disulfide isomerase family A, member 6 |
| 10682 | EBP | Emopamil binding protein (sterol isomerase) |
| 116844 | LRG1 | Leucine-rich alpha-2-glycoprotein 1 |
| 1209 | CLPTM1 | Cleft lip and palate associated transmembrane protein 1 |
| 132299 | OCIAD2 | OCIA domain containing 2 |
| 1528 | CYB5A | Cytochrome b5 type A (microsomal) |
| 154467 | C6orf129 | Chromosome 6 open reading frame 129 |
| 1571 | CYP2E1 | Cytochrome P450, family 2, subfamily E, polypeptide 1 |
| 196410 | METTL7B | Methyltransferase like 7B |
| 200185 | KRTCAP2 | Keratinocyte associated prteoin 2 |
| 2013 | EMP2 | Epithelial membrane protein 2 |
| 2147 | F2 | Coagulation factor II (thrombin) |
| 2220 | FCN2 | Ficolin (collagen/fibrinogen domain containing lectin) 2 (hucolin) |
| 2266 | FGG | Fibrinogen gamma chain |
| 2267 | FGL1 | Fibrinogen-like 1 |
| 27173 | SLC39A1 | Solute carrier family 39 (zinc transporter), member 1 |
| 2731 | GLDC | Glycine dehydrogenase (decarboxylating) |
| 286451 | YIPF6 | Yip1 domain family, member 6 |
| 334 | APLP2 | Amyloid beta (A4) precursor-like protein 2 |
| 335 | APOA1 | Apolipoprotein A-I |
| 338 | APOB | Apolipoprotein B (including Ag(x) antigen) |
| 3732 | CD82 | CD82 molecule |
| 4267 | CD99 | CD99 molecule |
| 4513 | COX2 | Cytochrome c oxidase subunit II |
| 4538 | ND4 | NADH dehydrogenase, subunit 4 (complex I) |
| 4924 | NUCB1 | Nucleobindin 1 |

TABLE 12-continued

| Gene ID | Symbol | Description of the Gene |
|---|---|---|
| 51075 | TMX2 | Thioredoxin-related transmembrane protein 2 |
| 51643 | TMBIM4 | Transmembrane BAX inhibitor motif containing 4 |
| 517 | ATP5G2 | ATP synthase, H+ transporting, mitochondrial F0 complex, subunit C2 (subunit 9) |
| 5265 | SERPINA1 | Serpin peptidase inhibitor, clade A (alpha-1 antiproteinase, antitrypsin), member 1 |
| 5355 | PLOP2 | Proteolipid protein 2 (colonic epithelium-enriched) |
| 5446 | PON3 | Praoxonase 3 |
| 54657 | UGT1A4 | UDP glucuronosyltransferase 1 family, polypeptide A4 |
| 54658 | UGT1A1 | UDP glucuronosyltransferase 1 family, polypeptide A1 |
| 5479 | PPIB | Peptidylprolyl isomerase B (cyclophilin B) |
| 563 | AZGP1 | Alpha-2-glycoprotein 1, zinc-binding |
| 56851 | C15orf24 | Chromosome 15 open reading frame 24 |
| 57817 | HAMP | Hepcidin antimicrobial peptide |
| 5950 | RBP4 | Retinol binding protein 4, plasma |
| 6048 | RNF5 | Ring finger protein 5 |
| 6522 | SLC4A2 | Solute carrier family 4, anion exchanger, member 2 (erythrocyte membrane protein band 3-like 1) |
| 7905 | REEP5 | Receptor accessory protein 5 |
| 84975 | MFSD5 | Major facilitator superfamily domain containing 5 |
| 9204 | ZMYM6 | Zinc finger, MYM-type 6 |
| 967 | CD63 | CD63 molecule |

Proteins that interacted with the above proteins were collected and added to the candidate genes. Using the protein-protein interaction information stored in the data warehouse, the processor collected 196 proteins that interacted with the proteins shown in Table 1 and 207 proteins that interacted with the proteins shown in Table 12. And, the processor added these collected genes to the candidate genes.

Therefore, the total candidate genes inputted were: (1) 207 proteins that interacted with HCV Core or that interacted with the proteins interacting with HCV Core, and (2) 252 proteins that interacted with HCV NS4B or that interacted with the proteins interacting with HCV NS4B. The lists of genes inputted are shown in Tables 13-15.

TABLE 13

(1) Proteins that Interact with Core or that Interact with the Proteins Interacting with Core

| Gene ID | Symbol | Gene ID | Symbol | Gene ID | Symbol | Gene ID | Symbol |
|---|---|---|---|---|---|---|---|
| 10014 | HDAC5 | 2885 | GRB2 | 526 | ATP6V1B2 | 6745 | SSR1 |
| 10060 | ABCC9 | 292 | SLC25A5 | 5265 | SERPINA1 | 6881 | TAF10 |
| 10289 | EIF1B | 293 | SLC25A6 | 5316 | PKNOX1 | 6885 | MAP3K7 |
| 10301 | DLEU1 | 2990 | GUSB | 5340 | PLG | 7077 | TIMP2 |
| 10381 | TUBB3 | 29900 | CCDC106 | 5347 | PLK1 | 7132 | TNFRSF1A |
| 10382 | TUBB4 | 3035 | HARS | 54984 | PINX1 | 7133 | TNFRSF1B |
| 10397 | NDRG1 | 3091 | HIF1A | 55068 | ENOX1 | 7185 | TRAF1 |
| 10425 | ARIH2 | 3106 | HLA-B | 55207 | ARL8B | 7186 | TRAF2 |
| 1053 | CEBPE | 3163 | HMOX2 | 55339 | WDR33 | 7189 | TRAF6 |
| 10563 | CXCL13 | 3189 | HNRNPH3 | 5562 | PRKAA1 | 7350 | UCP1 |
| 10574 | CCT7 | 3309 | HSPA5 | 5564 | PRKAB1 | 7407 | VARS |
| 10912 | GADD45G | 3329 | HSPD1 | 55743 | CHFR | 7414 | VCL |
| 11178 | LZTS1 | 335 | APOA1 | 55755 | CDK5RAP2 | 7416 | VDAC1 |
| 11345 | GABARAPL2 | 339448 | C1orf174 | 55803 | ADAP2 | 7428 | VHL |
| 116154 | PHACTR3 | 34 | ACADM | 5646 | PRSS3 | 7532 | YWHAG |
| 1200 | TPP1 | 347 | APOD | 5657 | PRTN3 | 7534 | YWHAZ |
| 126272 | EID2B | 354 | KLK3 | 566 | AZU1 | 7572 | ZNF24 |
| 1356 | CP | 3608 | ILF2 | 5682 | PSMA1 | 7579 | ZSCAN20 |
| 1478 | CSTF2 | 3692 | EIF6 | 5683 | PSMA2 | 7786 | MAP3K12 |
| 1511 | CTSG | 3735 | KARS | 5684 | PSMA3 | 78987 | CRELD1 |
| 1583 | CYP11A1 | 375 | ARF1 | 5685 | PSMA4 | 79008 | GIYD2 |
| 158345 | RPL4P5 | 3827 | KNG1 | 5686 | PSMA5 | 7917 | BAT3 |
| 1588 | CYP19A1 | 4035 | LRP1 | 5687 | PSMA6 | 7920 | BAT5 |
| 1647 | GADD45A | 4093 | SMAD9 | 5688 | PSMA7 | 79577 | CDC73 |
| 1736 | DKC1 | 412 | STS | 5695 | PSMB77 | 79676 | OGFOD2 |
| 1762 | DMWD | 4128 | MAOA | 56993 | TOMM22 | 79902 | NUP85 |
| 1891 | ECH1 | 4163 | MCC | 5710 | PSMD4 | 81502 | HM13 |
| 1933 | EEF1B2 | 4214 | MAP3K1 | 5717 | PSMD11 | 821 | CANX |
| 1936 | EEF1D | 427 | ASAH1 | 5719 | PSMD13 | 827 | CAPN6 |
| 1937 | EEF1G | 4353 | MPO | 57332 | CBX8 | 833 | CARS |
| 1942 | EFNA1 | 4543 | MTNR1A | 57562 | KIAA1377 | 84331 | FAM195A |
| 1956 | EGFR | 4597 | MVD | 5764 | PTN | 8440 | NCK2 |
| 1964 | EIF1AX | 4609 | MYC | 57664 | PLEKHA4 | 84651 | SPINK7 |
| 196549 | EEF1DP3 | 4704 | NDUFA9 | 5775 | SKIL | 8517 | IKBKG |
| 1983 | EIF5 | 4720 | NDUFS2 | 57761 | TRIB3 | 8717 | TRADD |
| 1991 | ELANE | 4722 | NDUFS3 | 5802 | PTPRS | 8737 | RIPK1 |
| 2 | A2M | 4729 | NDUFV2 | 5829 | PXN | 8767 | RIPK2 |
| 2023 | ENO1 | 4780 | NFE2L2 | 5863 | RGL2 | 9001 | HAP1 |
| 2035 | EPB41 | 4790 | NFKB1 | 596 | BCL2 | 9114 | ATP6V0D1 |
| 2108 | ETFA | 4792 | NFKBIA | 5970 | RELA | 9141 | PDCD5 |
| 2109 | ETFB | 4831 | NME2 | 5987 | TRIM27 | 9400 | RECQL5 |
| 2175 | FANCA | 498 | ATP5A1 | 60 | ACTB | 9446 | GSTO1 |
| 2237 | FEN1 | 5009 | OTC | 6124 | RPL4 | 9474 | ATG5 |
| 2290 | FOXG1 | 506 | ATP5B | 6234 | RPS28 | 950 | SCARB2 |
| 23557 | SNAPIN | 5071 | PARK2 | 6303 | SAT1 | 9540 | TP53I3 |
| 2495 | FTH1 | 51003 | MED31 | 6310 | ATXN1 | 9638 | FEZ1 |

TABLE 13-continued (1) Proteins that Interact with Core or that Interact with the Proteins Interacting with Core

| Gene ID | Symbol | Gene ID | Symbol | Gene ID | Symbol | Gene ID | Symbol |
|---|---|---|---|---|---|---|---|
| 251 | ALPPL2 | 51520 | LARS | 6399 | TRAPPC2 | 9641 | IKBKE |
| 2512 | FTL | 51535 | PPHLN1 | 64431 | ACTR6 | 9669 | EIF5B |
| 2597 | GAPDH | 51608 | C7orf20 | 6498 | SKIL | 9670 | IPO13 |
| 26085 | KLK13 | 51678 | MPP6 | 65220 | NADK | 9804 | TOMM20 |
| 2629 | GBA | 523 | ATP6V1A | 6613 | SUMO2 | 998 | CDC42 |
| 2720 | GLB1 | 5245 | PHB | 6633 | SNRPD2 | | |

TABLE 14

(2) Proteins that Interact with NS4B or that Interact with the Proteins Interacting with NS4B

| Gene ID | Symbol | Gene ID | Symbol | Gene ID | Symbol | Gene ID | Symbol |
|---|---|---|---|---|---|---|---|
| 10130 | PDIA6 | 2153 | F5 | 3674 | ITGA2B | 5479 | PPIB |
| 10307 | APBB3 | 2160 | F11 | 3683 | ITGAL | 54918 | CMTM6 |
| 10477 | UBE2E3 | 2165 | F13B | 3688 | ITGB1 | 54984 | PINX1 |
| 10612 | TRIM3 | 2189 | FANCG | 3690 | ITGB3 | 55034 | MOCOS |
| 10682 | EBP | 2220 | FCN2 | 3732 | CD82 | 5564 | PRKAB1 |
| 10747 | MASP2 | 2243 | FGA | 3815 | KIT | 55669 | MFN1 |
| 1080 | CFTR | 2244 | FGB | 3837 | KPNB1 | 55700 | MAP7D1 |
| 10924 | SMPDL3A | 2266 | FGG | 3857 | KRT9 | 55969 | C20orf24 |
| 10952 | SEC61B | 2267 | FGL1 | 3868 | KRT16 | 5617 | PRL |
| 10999 | SLC27A4 | 22861 | NLRP1 | 3929 | LBP | 563 | AZGP1 |
| 11061 | LECT1 | 23065 | KIAA0090 | 3931 | LCAT | 5635 | PRPSAP1 |
| 116844 | LRG1 | 23076 | RRP1B | 3990 | LIPC | 5646 | PRSS3 |
| 117854 | TRIM6 | 23460 | ABCA6 | 4035 | LRP1 | 5648 | MASP1 |
| 1191 | CLU | 24140 | FTSJ1 | 4163 | MCC | 5657 | PRTN3 |
| 1209 | CLPTM1 | 25777 | SUN2 | 4179 | CD46 | 56851 | C15orf24 |
| 1230 | CCR1 | 26049 | FAM169A | 4267 | CD99 | 5693 | PSMB5 |
| 128240 | APOA1BP | 26085 | KLK13 | 4513 | COX2 | 57003 | CCDC47 |
| 128876 | FAM83C | 267 | AMFR | 4538 | ND4 | 5738 | PTGFRN |
| 132299 | OCIAD2 | 27005 | USP21 | 4543 | MTNR1A | 5742 | PTGS1 |
| 132660 | LIN54 | 27173 | SLC39A1 | 4544 | MTNR1B | 5743 | PTGS2 |
| 1327 | COX4I1 | 2731 | GLDC | 4547 | MTTP | 57473 | ZNF512B |
| 1356 | CP | 2771 | GNAI2 | 4580 | MTX1 | 57599 | WDR48 |
| 1361 | CPB2 | 2810 | SFN | 462 | SERPINC1 | 57817 | HAMP |
| 15 | AANAT | 2811 | GP1BA | 4712 | NDUFB6 | 5829 | PXN |
| 1511 | CTSG | 2822 | GPLD1 | 4831 | NME2 | 5860 | QDPR |
| 1514 | CTSL1 | 286451 | YIPF6 | 4924 | NUCB1 | 5905 | RANGAP1 |
| 1528 | CYB5A | 29109 | FHOD1 | 4927 | NUP88 | 5950 | RBP4 |
| 154467 | C6orf129 | 29927 | SEC61A1 | 5037 | PEBP1 | 6048 | RNF5 |
| 1571 | CYP2E1 | 29946 | SERTAD3 | 5054 | SERPINE1 | 6146 | RPL22 |
| 1600 | DAB1 | 29979 | UBQLN1 | 51075 | TMX2 | 6185 | RPN2 |
| 1601 | DAB2 | 30061 | SLC40A1 | 5136 | PDE1A | 6289 | SAA2 |
| 1650 | DDOST | 302 | ANXA2 | 5142 | PDE4B | 633 | BGN |
| 1676 | DFFA | 3053 | SERPIND1 | 51465 | UBE2J1 | 64221 | ROBO3 |
| 1785 | DNM2 | 3106 | HLA-B | 51497 | TH1L | 6462 | SHBG |
| 1791 | DNTT | 3109 | HLA-DMB | 516434 | TMBIM4 | 64759 | TNS3 |
| 1839 | HBEGF | 3112 | HLA-DOB | 517 | ATP5G2 | 6522 | SLC4A2 |
| 1876 | E2F6 | 3122 | HLA-DRA | 5265 | SERPINA1 | 6667 | SP1 |
| 19 | ABCA1 | 3164 | NR4A1 | 5269 | SERPINB6 | 672 | BRCA1 |
| 1956 | EGFR | 319 | APOF | 5327 | PLAT | 6722 | SRF |
| 196410 | METTL7B | 3191 | HNRNPL | 5355 | PLP2 | 6745 | SSR1 |
| 1991 | ELANE | 322 | APBB1 | 5360 | PLTP | 6748 | SSR4 |
| 200185 | KRTCAP2 | 3276 | PRMT1 | 54065 | FAM165B | 6775 | STAT4 |
| 2013 | EMP2 | 3312 | HSPA8 | 54205 | CYCS | 6836 | SURF4 |
| 202559 | KHDRBS2 | 334 | APLP2 | 5446 | PON3 | 7018 | TF |
| 2064 | ERBB2 | 335 | APOA1 | 5447 | POR | 7056 | THBD |
| 2065 | ERBB | 338 | APOB | 54499 | TMCO1 | 7057 | THBS1 |
| 213 | ALB | 341 | APOC1 | 54532 | USP53 | 7076 | TIMP1 |
| 2147 | F2 | 345 | APOC3 | 54657 | UGT1A4 | 710 | SERPING1 |
| 2149 | F2R | 351 | APP | 54658 | UGT1A1 | 712 | C1QA |
| 2150 | F2RL1 | 354 | KLK3 | 5478 | PPIA | 7128 | TNFAIP3 |

TABLE 15

(2) Proteins that Interact with NS4B or that Interact with the Proteins Interacting with NS4B

| Gene ID | Symbol | Gene ID | Symbol | Gene ID | Symbol | Gene ID | Symbol |
|---|---|---|---|---|---|---|---|
| 714 | C1QC | 78992 | YIPF2 | 8574 | AKR7A2 | 93185 | IGSF8 |
| 7184 | HSP90B1 | 7905 | REEP5 | 8708 | B3GALT1 | 9319 | TRIP13 |
| 7185 | TRAF1 | 79139 | DERL1 | 8764 | TNFRSF14 | 9377 | COX5A |
| 7189 | TRAF6 | 7920 | BAT5 | 8794 | TNFRSF10C | 94101 | ORMDL1 |
| 7248 | TSC1 | 799 | CALCR | 8848 | TSC22D1 | 959 | CD40LG |
| 7276 | TTR | 811 | CALR | 8858 | PROZ | 9601 | PDIA4 |
| 7295 | TXN | 81839 | VANGL1 | 8879 | SGPL1 | 9641 | IKBKE |
| 7322 | UBE2D2 | 819 | CAMLG | 90293 | KLHL13 | 9667 | SAFB2 |
| 7323 | UBE2D3 | 821 | CANX | 91107 | TRIM47 | 967 | CD63 |
| 7324 | UBE2E1 | 84650 | EBPL | 9146 | HGS | 977 | CD151 |
| 7328 | UBE2H | 84975 | MFSD5 | 920 | CD4 | 9804 | TOMM20 |
| 7428 | VHL | 8518 | IKBKAP | 9204 | ZMYM6 | 9852 | EPM2AIP1 |
| 7448 | VTN | 8542 | APOL1 | 928 | CD9 | 93185 | IGSF8 |

Next, the processor executed the gathering step and collected the annotations assigned to the proteins inputted. Table 16 shows the number of gathered annotations as well as the annotations that were assigned to the candidate genes statistically significantly more than to the control genes and that gave p≤0.05 by hypothesis test.

TABLE 16

| | the Gene Ontology | KEEG Pathway | OMIM | Disease Ontology |
|---|---|---|---|---|
| (1) Core | | | | |
| Annotations Gathered | 750 annotations | 456 annotations | 81 annotations | 1134 annotations |
| | 454 types | 122 types | 78 types | 434 types |
| Statistically Significant Annotations (p ≤ 0.05) | 77 types | 24 types | 54 types | 320 types |
| (2) NS4B | | | | |
| Annotations Gathered | 958 annotations | 396 annotations | 105 annotations | 1787 annotations |
| | 572 types | 113 types | 100 types | 582 types |
| Statistically Significant Annotations (p ≤ 0.05) | 43 types | 3 types | 63 types | 484 types |

The processor executed a choosing step and chose top 10 annotations, whose p-values were smallest, from the above annotations. Then, the processor executed a selection step and selected proteins. In this step, the processor selected the proteins at least to which Core or NS4B was assigned as an annotation in the protein-protein interaction information so that the selected proteins would be likely to interact with Core or NS4B. The proteins selected by the selection step are shown in Table 17.

TABLE 17

| | the Gene Ontology | KEEG Pathway | OMIM | Disease Ontology |
|---|---|---|---|---|
| (1) Core | | | | |
| Proteins Selected | NDUFS2, PSMA7, SLC25A5 | PSMA7 | | ENO1 |

TABLE 17-continued

| | the Gene Ontology | KEEG Pathway | OMIM | Disease Ontology |
|---|---|---|---|---|
| (2) NS4B | | | | |
| Proteins Selected | F2, FGG, SERPINA1 | APOA1, APOB, F2, RBP4 | APOA1, APOB, UGT1A1 | APOA1, APOB, AZGP1, CD82, COX2, F2, FGG, GLDC, |

Figure 3:
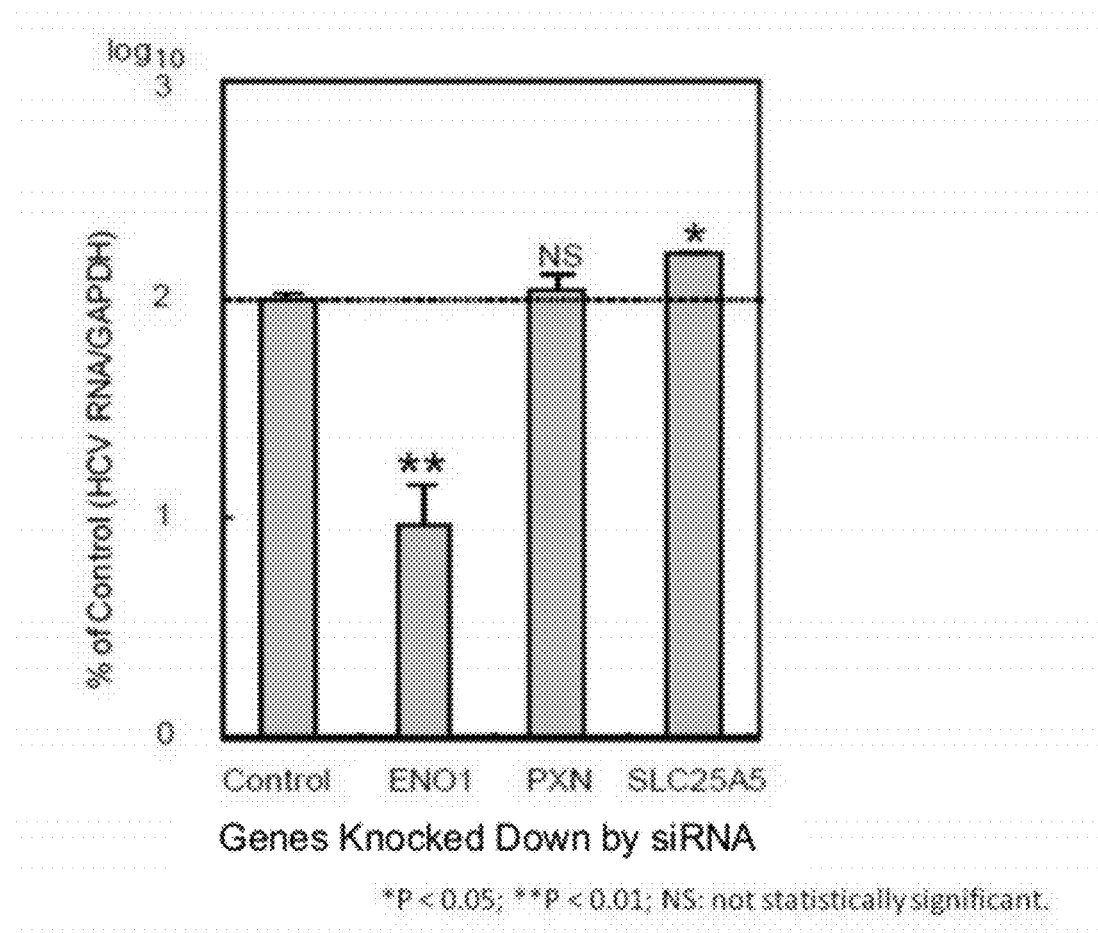
FIG. 3 is a graph showing the result of experiment that tested whether the genes selected by the present invention were relevant to an onset of hepatitis C.

To confirm whether the genes selected were relevant to the onset of hepatitis C, experiments were conducted for SLC25A5 and ENO1 selected from the genes listed in Table 17. Experiments were also conducted for PXN, which was the protein that interacted with both SLC25A5 and ENO1. siR-NAs against SLC25A5, ENO1 and PXN were introduced into Huh7OK1 cells. 24 hours later, the Huh7OK1 cells were made infected by a hepatitis C virus strain JFH-1 (genotype 2a). After infection, the cells were cultured for 72 hours. The viral RNA contained in the supernatant of the medium and the GAPDH mRNA contained in the cells were measured by quantitative real time RT-PCR. The ratio of the viral RNA to the GAPDH mRNA is shown in FIG. 3. The amount of the viral RNA in the medium was significantly decreased by the knockdown of ENO1. The amount of the viral RNA was increased by the knockdown of SLC25A5 statistically significantly ($p<0.01$). However, in the knockdown of PXN, statistically significant difference was not observed for the amount of the viral RNA.

Figure 4:
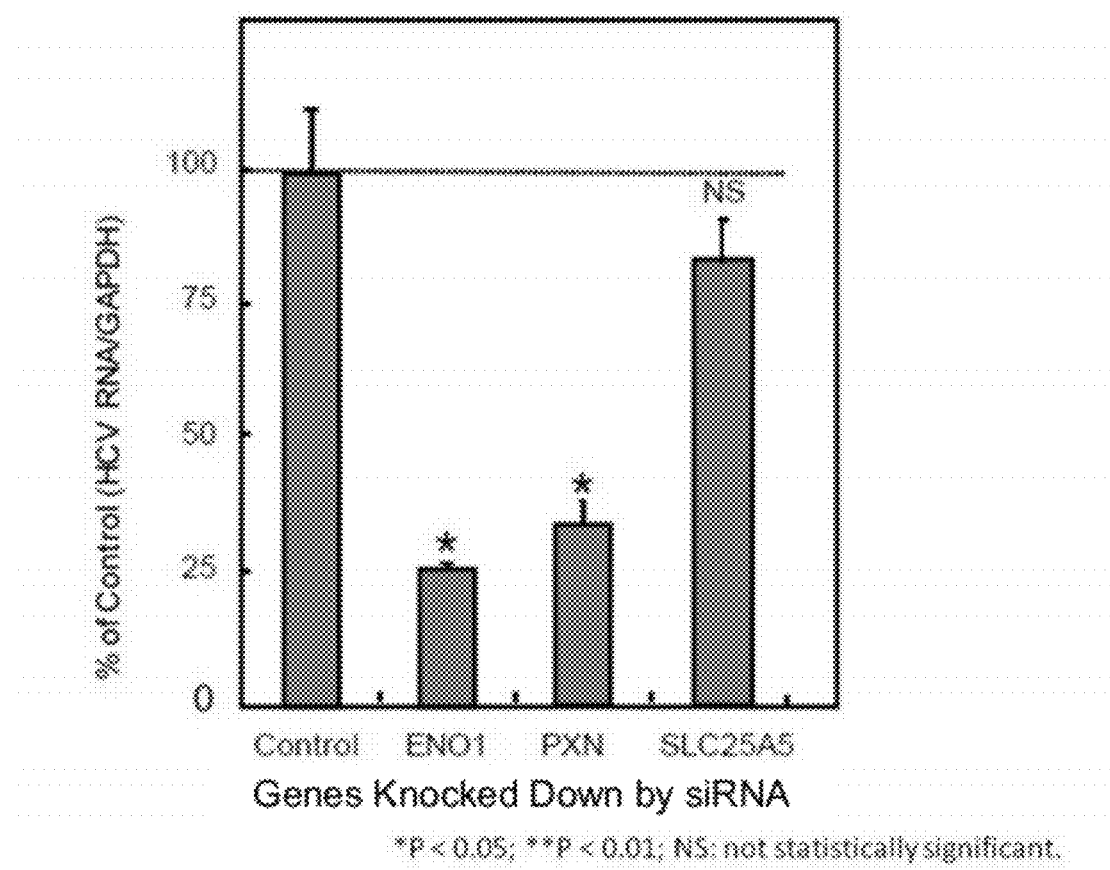
FIG. 4 is a graph showing the result of experiment that tested whether the genes selected by the present invention were relevant to an onset of hepatitis C.

To study the effect of the selected genes to other genotype of hepatitis C virus, the same siRNAs were respectively introduced to Huh-7 cells containing an HCV replicon derived from JFH-1 (genotype 2a) and Con-1 (genotype 1b). Then, the amount of Con-1 viral RNA in the supernatant of the medium and the amount of GAPDH mRNA in the cell were measured by quantitative real time RT-PCR. The ratio of the Con-1 viral RNA amount to the GAPDH mRNA amount is shown in FIG. 4. The replication of HCV Con-1 was suppressed by the knockdowns of ENO1 and PXN.

The above experiments revealed that SLC25A5, ENO1 and PXN are the proteins involved in the replication of HCV. Therefore, it was found that SLC25A5, ENO1 and PXN, selected by the present invention from a large number of the candidate genes, are relevant to the onset of hepatitis C.

INDUSTRIAL APPLICABILITY

The device, method and computer program of the present invention can contribute to a discovery of a novel relation between a gene and a disease as well as a development of a new drug.

The invention claimed is:

1. A device for selecting genes or proteins relevant to a specific function from a set of candidate genes or proteins without supervised machine learning or positive and negative examples, the device comprising:
    a storage device that stores a data about a collection of genes or proteins, with which annotations are associated;
    an input device that receives an input of the set of candidate genes or proteins; and
    a processor that:
        (a) gathers annotations that are associated with the candidate genes or proteins inputted, the annotations being gathered from the storage device;
        (b) chooses annotations that are associated with the candidate genes or proteins more than a threshold number of times or frequencies, the annotations being chosen from the annotations gathered, wherein the threshold number of times or frequencies are selected from the group consisting of:
            (i) a threshold number of times or frequencies determined by the processor, wherein the processor determines the threshold number of times or frequencies so that the number of times or frequencies the annotation is associated with the candidate genes or proteins is larger than a number of times or frequencies the annotation is associated with control genes or proteins; and
            (ii) a threshold number of times or frequencies determined by the processor, wherein the processor determines the threshold number of times or frequencies so that the number of times or frequencies the annotation is associated with the candidate genes or proteins is larger than a number of times or frequencies the annotation is associated with control genes or proteins with statistical significance, and a p-value provided by a statistical significance test comparing the number of times or frequencies the annotation is associated with the candidate genes or proteins to the number of times or frequencies the annotation is associated with the control genes or proteins is less than a predetermined value; and
        (c) selects genes or proteins, with which at least one of the chosen annotations is associated, the genes or proteins being selected from the set of candidate genes or proteins inputted without supervised machine learning or positive and negative examples, wherein the selected genes or proteins are considered having relevancy to the specific function from the set of candidate genes or proteins.

2. The device of claim 1, further comprising an output device that outputs the genes or proteins selected by the processor.

3. The device of claim 2:
    wherein the storage device is a hard disk drive;
    wherein the input device is a keyboard or a mouse;
    wherein the processor is a central processing unit;
    wherein the output device is a display or a printer; and
    wherein the hard disk drive, the keyboard or the mouse, the central processing unit and the display or the printer are installed in or connected to a computer, which constitutes the device.

4. The device of claim 1, the processor chooses annotations so that the chosen annotations include an annotation that is associated with the candidate genes or proteins a largest number of times or frequencies.

5. The device of claim 1, the processor chooses annotations so that the chosen annotations include an annotation that gives a largest difference between a number of times or frequencies the annotation is associated with the candidate genes or proteins and a number of times or frequencies the annotation is associated with the control genes or proteins.

6. The device of claim 1, the processor chooses annotations so that the chosen annotations include an annotation that has a smallest p-value provided by a statistical significance test comparing the number of times or frequencies the annotation is associated with the candidate genes or proteins to the number of times or frequencies the annotation is associated with the control genes or proteins.

7. The device of claim 1, wherein the control genes or proteins are a collection of genes or proteins derived from a tissue or an organism.

8. The device of claim 1, wherein the processor ranks or sorts the selected genes or proteins based on a number of the chosen annotations for each of the genes or proteins.

9. The device of claim 8, wherein the processor weighs the chosen annotation based on a number of times or frequencies the annotation is associated with the candidate genes or proteins.

10. The device of claim 8, wherein the processor weighs the chosen annotation based on a difference between a number of times or frequencies the annotation is associated with the candidate genes or proteins and a number of times or frequencies the annotation is associated with the control genes or proteins.

11. The device of claim 1, wherein the processor removes redundant annotations before choosing annotations.

12. The device of claim 1, wherein the processor converts formats of the gathered annotations to other formats before choosing annotations.

13. The device of claim 1, wherein the processor obtains a gene or protein that interacts with the candidate gene or protein, and the processor adds the obtained gene or protein to the set of candidate genes or proteins.

14. The device of claim 1, wherein the processor obtains a gene or protein corresponding to the candidate gene or protein, the gene or protein belonging to a species different from a species of the candidate gene or protein, and the processor adds the obtained gene or protein to the set of candidate genes or proteins.

15. The device of claim 1, wherein the annotations are related to biological information selected from the group consisting of: gene information, gene homology information, genetic polymorphism information, gene expression information, protein information, protein-protein interaction information, information on biological functions of proteins, protein domain information, protein structure information, protein expression information, enzyme function information, pathway information, transcription factor information, information about genes that relate to diseases or disorders or that cause diseases or disorders, drug information, and compound information.

16. A method of selecting genes or proteins relevant to a specific function from a set of candidate genes or proteins without supervised machine learning or positive and negative examples, the method being performed by a computer and the method comprising the steps of:
  (1) receiving an input of the set of candidate genes or proteins;
  (2) accessing a data warehouse or database that contains a data about a collection of genes or proteins, with which annotations are associated;
  (3) gathering annotations that are associated with the candidate genes or proteins inputted, the annotations being gathered from the data warehouse or database;
  (4) choosing annotations that are associated with the candidate genes or proteins more than a threshold number of times or frequencies, the annotations being chosen from the annotations gathered, wherein the threshold number of times or frequencies are selected from the group consisting of:
    (i) a threshold number of times or frequencies determined by the computer, wherein the computer determines the threshold number of times or frequencies so that the number of times or frequencies the annotation is associated with the candidate genes or proteins is larger than a number of times or frequencies the annotation is associated with control genes or proteins; and
    (ii) a threshold number of times or frequencies determined by the computer, wherein the computer determines the threshold number of times or frequencies so that the number of times or frequencies the annotation is associated with the candidate genes or proteins is larger than a number of times or frequencies the annotation is associated with control genes or proteins with statistical significance, and a p-value provided by a statistical significance test comparing the number of times or frequencies the annotation is associated with the candidate genes or proteins to the number of times or frequencies the annotation is associated with the control genes or proteins is less than a predetermined value; and
  (5) selecting genes or proteins, with which at least one of the chosen annotations is associated, the genes or proteins being selected from the set of candidate genes or proteins inputted without supervised machine learning or positive and negative examples, wherein the selected genes or proteins are considered having relevancy to the specific function from the set of candidate genes or proteins.

17. A computer program product for selecting genes or proteins relevant to a specific function from a set of candidate genes or proteins without supervised machine learning or positive and negative examples, the computer program product comprising instructions, encoded in a non-transitory computer readable medium, for causing a computer to perform operations of:
  (1) receiving the set of candidate genes or proteins;
  (2) accessing a data warehouse or database that contains a data about a collection of genes or proteins, with which annotations are associated;
  (3) gathering annotations that are associated with the candidate genes or proteins received, the annotations being gathered from the data warehouse or database;
  (4) choosing annotations that are associated with the candidate genes or proteins more than a threshold number of times or frequencies, the annotations being chosen from the annotations gathered, wherein the threshold number of times or frequencies are selected from the group consisting of:
    (i) a threshold number of times or frequencies determined by the computer program product, wherein the computer program product determines the threshold number of times or frequencies so that the number of times or frequencies the annotation is associated with the candidate genes or proteins is larger than a number of times or frequencies the annotation is associated with control genes or proteins; and
    (ii) a threshold number of times or frequencies determined by the computer program product, wherein the computer program product determines the threshold number of times or frequencies so that the number of times or frequencies the annotation is associated with the candidate genes or proteins is larger than a number of times or frequencies the annotation is associated with control genes or proteins with statistical significance, and a p-value provided by a statistical significance test comparing the number of times or frequencies the annotation is associated with the candidate genes or proteins to the number of times or frequencies the annotation is associated with the control genes or proteins is less than a predetermined value; and
  (5) selecting genes or proteins, with which at least one of the chosen annotations is associated, the genes or proteins being selected from the set of candidate genes or proteins received without supervised machine learning or positive and negative examples, wherein the selected genes or proteins are considered having relevancy to the specific function from the set of candidate genes or proteins.

* * * * *